(12) United States Patent
Miyamoto et al.

(10) Patent No.: US 8,092,371 B2
(45) Date of Patent: Jan. 10, 2012

(54) MEDICAL TREATMENT ENDOSCOPE

(75) Inventors: Manabu Miyamoto, Tokyo (JP);
Takahiro Kogasaka, Tokyo (JP);
Takumi Dejima, Tokyo (JP); Kiyotaka Matsuno, Sagamihara (JP); Ken Yamatani, Tokyo (JP); Saori Takeuchi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1219 days.

(21) Appl. No.: 11/331,963

(22) Filed: Jan. 13, 2006

(65) Prior Publication Data

US 2007/0167679 A1    Jul. 19, 2007

(51) Int. Cl.
*A61B 1/00* (2006.01)
(52) U.S. Cl. .......................................... 600/106; 600/104
(58) Field of Classification Search .................. 600/104, 600/106, 107, 113, 118, 139–144, 146, 114, 600/145, 149; 606/205–209, 201, 225
See application file for complete search history.

(56) References Cited

U.S. PATENT DOCUMENTS

| | | | |
|---|---|---|---|
| 4,577,621 A | 3/1986 | Patel | |
| 4,873,965 A | 10/1989 | Danieli | |
| 5,318,013 A | 6/1994 | Wilk | |
| 5,395,367 A | 3/1995 | Wilk | |
| 5,448,989 A | 9/1995 | Heckele | |
| 5,683,349 A | 11/1997 | Makower et al. | |
| 5,916,147 A | 6/1999 | Boury | |
| 5,976,075 A | 11/1999 | Beane et al. | |
| 6,013,024 A | 1/2000 | Mitsuda et al. | |
| 6,352,503 B1 | 3/2002 | Matsui et al. | |
| 6,780,151 B2 | 8/2004 | Grabover et al. | |
| 2002/0087048 A1 | 7/2002 | Brock et al. | |
| 2004/0044270 A1 | 3/2004 | Barry | |
| 2004/0117032 A1* | 6/2004 | Roth | 623/23.72 |
| 2004/0138525 A1 | 7/2004 | Saadat et al. | |
| 2004/0138529 A1* | 7/2004 | Wiltshire et al. | 600/144 |
| 2004/0193212 A1 | 9/2004 | Taniguchi et al. | |
| 2005/0065397 A1 | 3/2005 | Saadat et al. | |
| 2005/0075538 A1 | 4/2005 | Banik et al. | |
| 2005/0119522 A1 | 6/2005 | Okada | |

(Continued)

FOREIGN PATENT DOCUMENTS

EP         1 872 709 A1      1/2008

(Continued)

OTHER PUBLICATIONS

U.S. Office Action dated Feb. 1, 2011 received in related U.S. Appl. No. 11/809,488.

(Continued)

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

The medical treatment endoscope according to the present invention includes a sheath having a flexibility; at least one arm member having a bending part that projects out from a front end of the sheath and performs bending actions; an open/close mechanism which directs the arm member from a direction along a central axis of the sheath to a direction deviated from the central axis of the sheath, and from a direction deviated from the central axis of the sheath to a direction along the central axis of the sheath; and a viewing device and an illuminating member that are disposed to the front end side of the sheath.

10 Claims, 21 Drawing Sheets

U.S. PATENT DOCUMENTS

| | | |
|---|---|---|
| 2005/0222495 A1 | 10/2005 | Okada et al. |
| 2005/0228224 A1 | 10/2005 | Okada et al. |
| 2005/0234294 A1* | 10/2005 | Saadat et al. ................. 600/104 |
| 2005/0234296 A1* | 10/2005 | Saadat et al. ................. 600/129 |
| 2005/0250989 A1 | 11/2005 | Suzuki et al. |
| 2006/0111615 A1 | 5/2006 | Danitz et al. |
| 2007/0004967 A1 | 1/2007 | Ueno et al. |
| 2007/0156019 A1 | 7/2007 | Larkin et al. |
| 2007/0167679 A1 | 7/2007 | Miyamoto et al. |
| 2007/0167680 A1 | 7/2007 | Miyamoto et al. |
| 2007/0232856 A1 | 10/2007 | Ueno et al. |
| 2007/0299387 A1 | 12/2007 | Williams et al. |
| 2008/0051631 A1 | 2/2008 | Dejima et al. |

FOREIGN PATENT DOCUMENTS

| | | |
|---|---|---|
| EP | 1 967 123 A1 | 9/2008 |
| JP | 55-45436 | 3/1980 |
| JP | 56-104501 | 8/1981 |
| JP | 63-102401 | 7/1988 |
| JP | 5-49594 | 3/1993 |
| JP | 8-131441 | 5/1996 |
| JP | 10-258022 | 9/1998 |
| JP | 11-318815 A | 11/1999 |
| JP | 2004-180781 | 7/2004 |
| JP | 2004-290569 | 10/2004 |
| JP | 2005-287963 | 10/2005 |
| JP | 2005-296412 | 10/2005 |
| JP | 2006-516910 | 7/2006 |
| JP | 2007-151595 | 6/2007 |
| JP | 2007-175070 | 7/2007 |
| JP | 2007-275624 | 10/2007 |
| WO | WO 2004/064600 A2 | 8/2004 |
| WO | WO 2007/057880 A2 | 5/2007 |
| WO | WO 2007/074571 A1 | 7/2007 |
| WO | WO 2007/080974 A1 | 7/2007 |

OTHER PUBLICATIONS

U.S. Office Action dated Mar. 24, 2010, received in related U.S. Appl. No. 11/435,183.

U.S. Office Action dated Jul. 9, 2010.

U.S. Office Action dated Mar. 2, 2011 received in related U.S. Appl. No. 11/652,880.

U.S. Office Action dated Mar. 16, 2011 received in related U.S. Appl. No. 11/435,183.

Office Action dated Oct. 5, 2011 from corresponding U.S. Appl. No. 11/652,880.

* cited by examiner

MEDICAL TREATMENT ENDOSCOPE

BACKGROUND OF THE INVENTION

1. Field of the Invention

The present invention relates to a medical treatment endoscope.

2. Description of Related Art

Laparoscopic operations are known in which, in performing a medical procedure of observing, treating, etc. an organ of the human body, instead of incising the abdominal wall widely, a plurality of orifices are opened in the abdominal wall and procedures are performed upon inserting a laparoscope, forceps, and other treatment instruments into the orifices. Such procedure provides the benefit of lessening the burden placed on the patient because only small orifices need to be opened in the abdominal wall.

In recent years, methods of performing procedures upon inserting a flexible endoscope via the mouth, nose, anus, or other natural orifice of the patient have been proposed as methods of further reducing the burden on the patient. An example of a medical treatment endoscope used in such procedures is disclosed in U.S. Patent Application Publication No. 2005/0065397.

In the medical treatment endoscope disclosed in this reference, arm members that have a bendable end are respectively inserted into a plurality of lumens disposed within a flexible inserted part that is inserted into the body via the mouth of the patient. By inserting respective instruments through these arm members, the procedure site can be approached from different directions with the various instruments. Accordingly, a plurality of procedures can be carried out in continuum by means of a single endoscope inserted into the body.

SUMMARY OF THE INVENTION

The medical treatment endoscope according to a first aspect of the present invention includes a sheath having a flexibility; at least one arm member having a bending part that projects out from a front end of the sheath and performs bending actions; an open/close mechanism which directs the arm member from a direction along a central axis of the sheath to a direction deviated from the central axis of the sheath, and from a direction deviated from the central axis of the sheath to a direction along the central axis of the sheath; and a viewing device and an illuminating member that are disposed to the front end side of the sheath.

The medical treatment endoscope according to a second aspect of the present invention includes a sheath having a flexibility, in which a first lumen with an open end is formed; at least one arm member having a second lumen with an open-end extending in the axial direction into which a procedure device for performing a procedure in an organ is insertable, and a bending part for performing bending actions, a front end of the arm member projecting out from the open end of the first lumen; an open/close mechanism which directs the arm member projecting out from the first lumen from a direction along the central axis of the sheath to a direction deviated from the central axis of the sheath, and from a direction deviated from the central axis of the sheath to a direction along the central axis of the sheath; and a viewing device and an illuminating member that are disposed to a front end side of the sheath.

The medical treatment endoscope according a third aspect of the present invention includes a first sheath having a flexibility and an open end; a second sheath that is provided with a first arm member that has a front end and a base end and is inserted so that the front end area projects out from the first sheath, and that has a bending part that is freely bending through manipulation by an operator; a third sheath provided with a second arm member that has a front end and a base end and is inserted so that the front end region projects out from the first sheath, and that has a bending part that is freely bending through manipulation by the operator; a viewing device that is independently disposed at the front end of the first sheath from the second sheath and the third sheath, and is for viewing a target image; and an illuminating member that is independently disposed at the front end of the first sheath from the viewing device, the second sheath and the third sheath, and is for radiating illuminating light on the target image.

The medical treatment endoscope according to a third aspect of the present invention includes a sheath having a flexibility; an arm means that projects out from the end of the sheath and is for performing bending actions; an open/close means which directs the arm means from a direction along a central axis of the sheath to a direction deviated from the central axis of the sheath, and from a direction deviated from the central axis of the sheath to the direction of the central axis of the sheath; a viewing means for viewing an area further toward the front end than the sheath; and an advance/retract means for advancing or retracting the arm means with respect to the sheath.

DETAILED DESCRIPTION OF THE INVENTION

Embodiments according to the present invention will now be described in detail below. In the following description, components that are the same shall be provided with the same numeric symbol and redundant description shall be omitted.

First Embodiment

Figure 1:
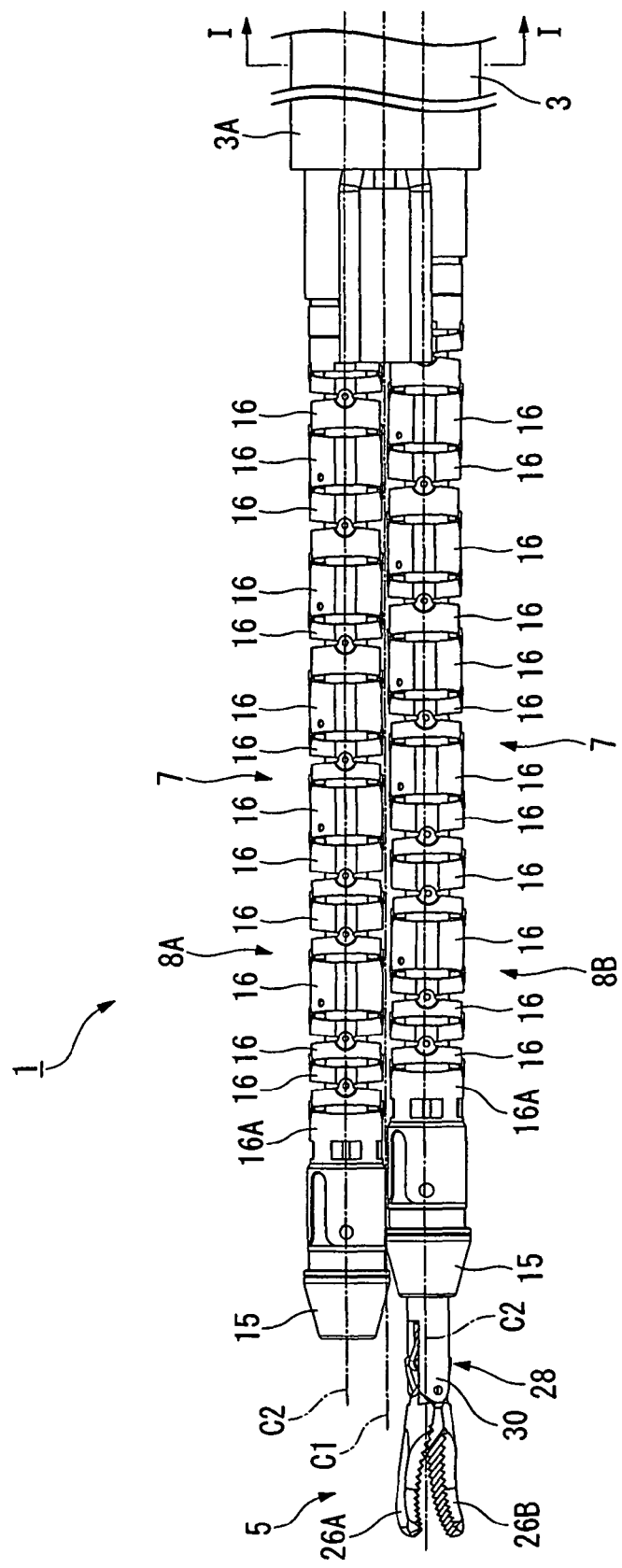
FIG. 1 is a view showing the structure of the front end of the medical treatment endoscope according to the first embodiment.
Figure 2A:
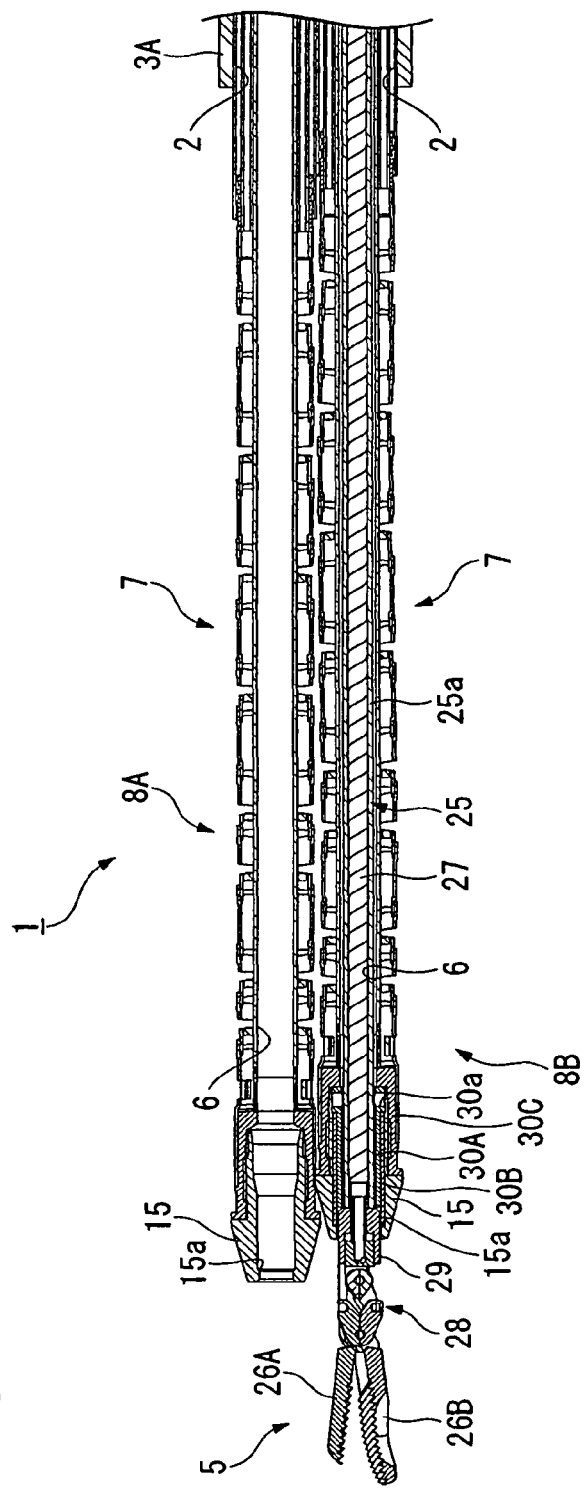
FIG. 2A is a cross-sectional view showing the structure of the front end of the medical treatment endoscope according to the first embodiment.
Figure 2B:
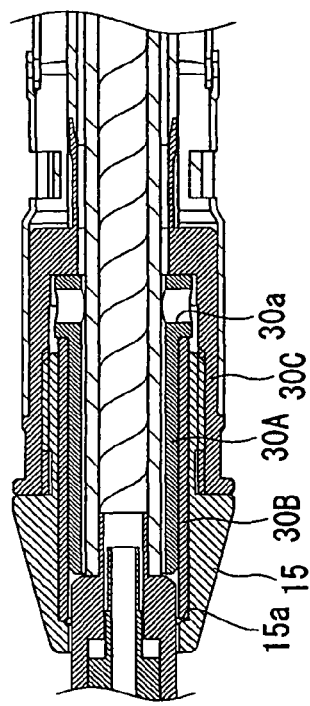
FIG. 2B is an enlarged view of the essential elements in FIG. 2A.
Figure 3:
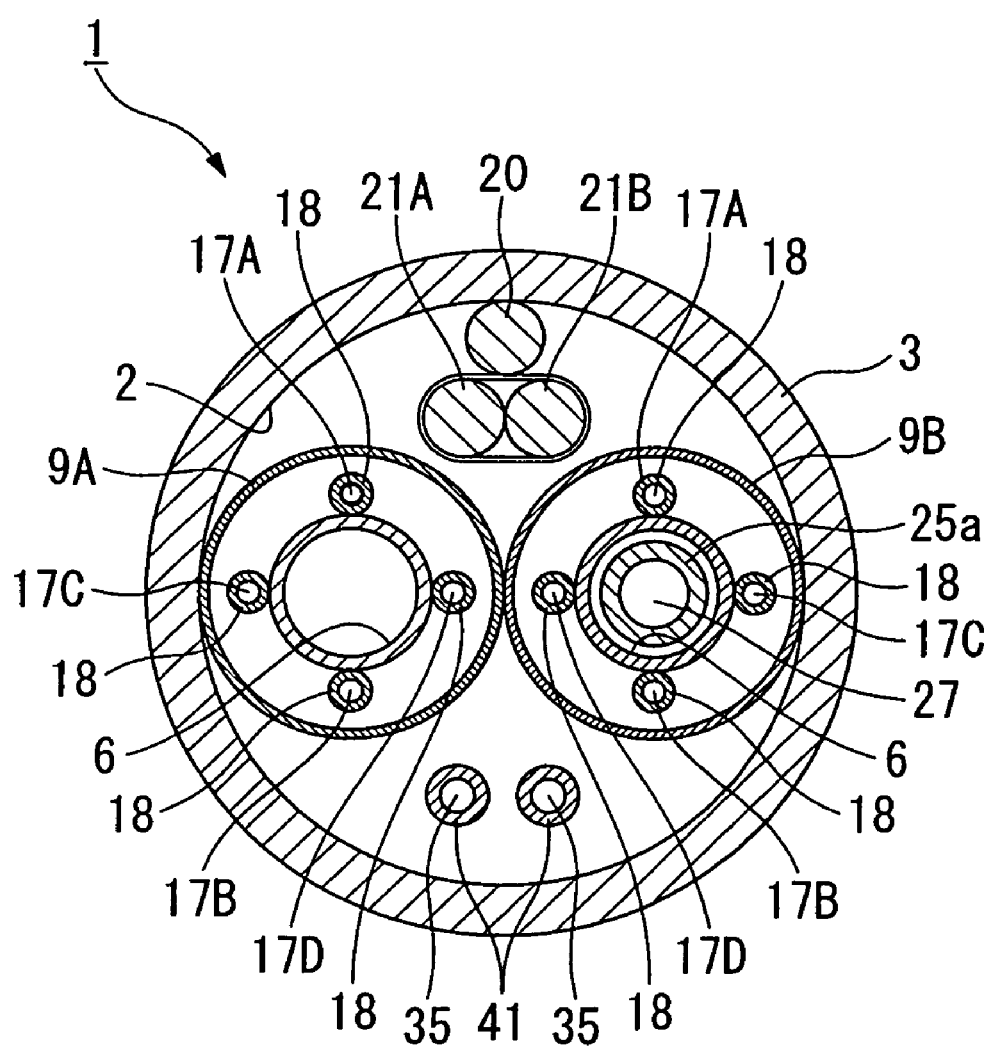
FIG. 3 is a cross-sectional view along the line I-I in FIG. 1.
Figure 4:
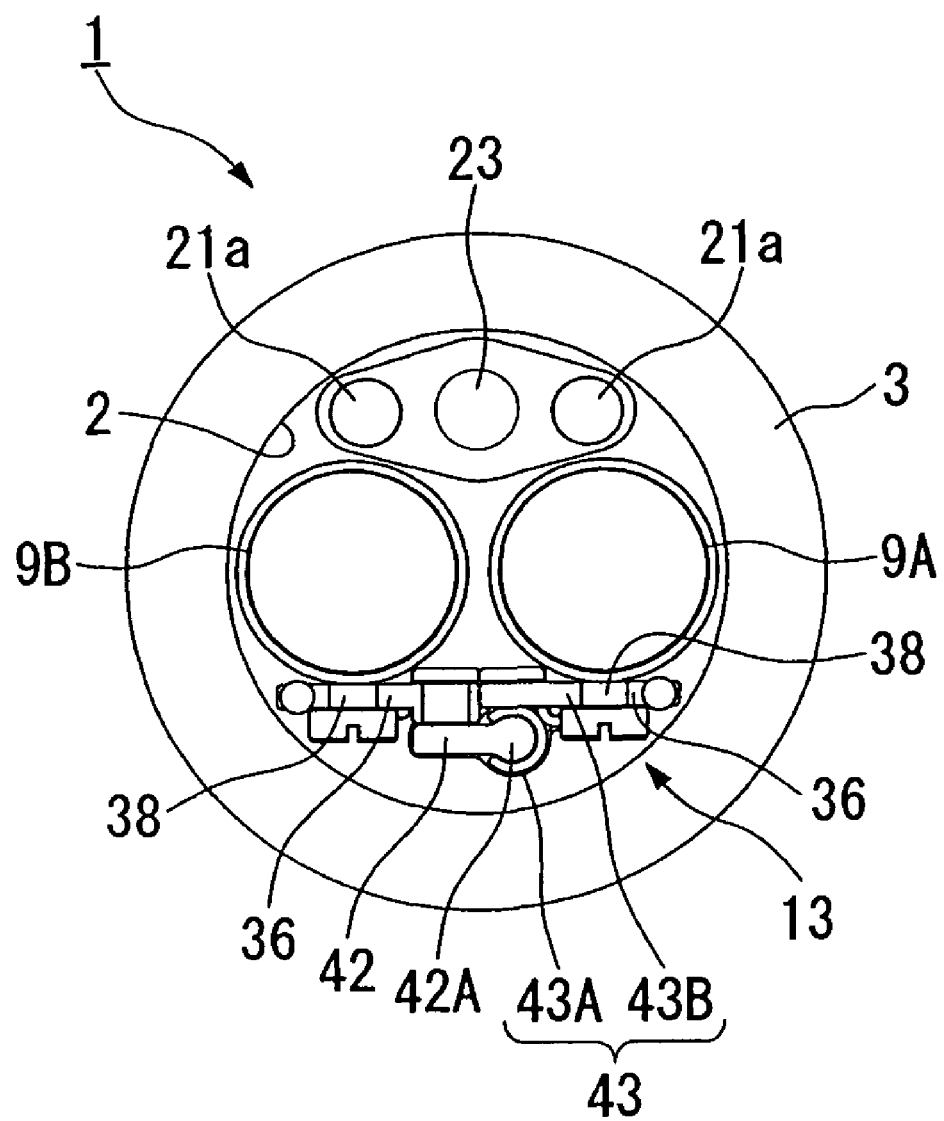
FIG. 4 is a view of the front end of the medical treatment endoscope according to the first embodiment.

As shown in FIGS. 1 through 3, the medical treatment endoscope 1 according to this embodiment is provided with a flexible first sheath (sheath) 3 in which an open-ended first lumen 2 is formed; a second sheath 9A having a first arm member 8A to which is disposed an open-ended instrument insertion channel (second lumen) 6 into which instruments such as gripping forceps 5 are inserted, and a bending part 7 that projects out from the first sheath 3 and carries out bending actions; and a third sheath 9B having a second arm member 8B to which the instrument insertion channel 6 and the bending part 7 are disposed. Moreover, as shown in FIGS. 4 through 8B, the medical treatment endoscope I according to this embodiment is further provided with an open/close mechanism 10 for changing the inclination of the first arm member 8A and the second arm member 8B that project out from the first sheath 3, from the central axis C1 of the first sheath 3 to a direction away from the central axis C1, and from this direction away from the central axis C1 toward the direction of the central axis C1 (separation release); a viewing device 12 that is disposed to the front end side of the first sheath 3; and an advance/retract mechanism 13 for advancing and retracting the first arm member 8A with respect to the first sheath 3.

The second sheath 9A has a front end and a base end, the front end region forming the first arm member 8A. The second sheath 9A is inserted into the first lumen 2 so as to project out from the first sheath 3, at a position in the first lumen 2 so as to appear on the right side of the viewing screen. The third sheath 9B has a front end and a base end, the front end region forming the second arm member 8B. The third sheath 9B is inserted into the first lumen 2 adjacent to the second sheath 9A, so as to project out from the first sheath 3.

As shown in FIGS. 1 and 2, rigid front end parts 15 are disposed to the front ends of the first arm member 8A and the second arm member 8B. A bumper 15a is provided to the front end part 15 for limiting movement in the forward direction when gripping forceps 5 or the like are inserted from the base end side of the instrument insertion channel 6.

As in the case of the typical flexible endoscope, the bending part 7 is designed such that a plurality of joint wheels 16 are mutually axially supported to enable rotation, and are connected along the direction of the central axis C2 of the first arm member 8A and the second arm member 8B. Furthermore, bending wires 17A, 17B, 17C, and 17D such as shown in FIG. 3, are connected to the joint wheel 16A that is disposed farthest toward the front end. Bending wires 17A, 17B, 17C, and 17D are each inserted into and pass through the joint wheels 16 at positions so as to divide the circumferential periphery of the joint wheels 16 into quarters. Bending wires 17A and 17B, and bending wires 17C and 17D are paired respectively, and positioned so as to be symmetrical about the center of bending part 7. Each bending wire 17A, 7B, 17C, and 17D is inserted into a bending wire coil 18 within the first sheath 3.

Figure 7A:
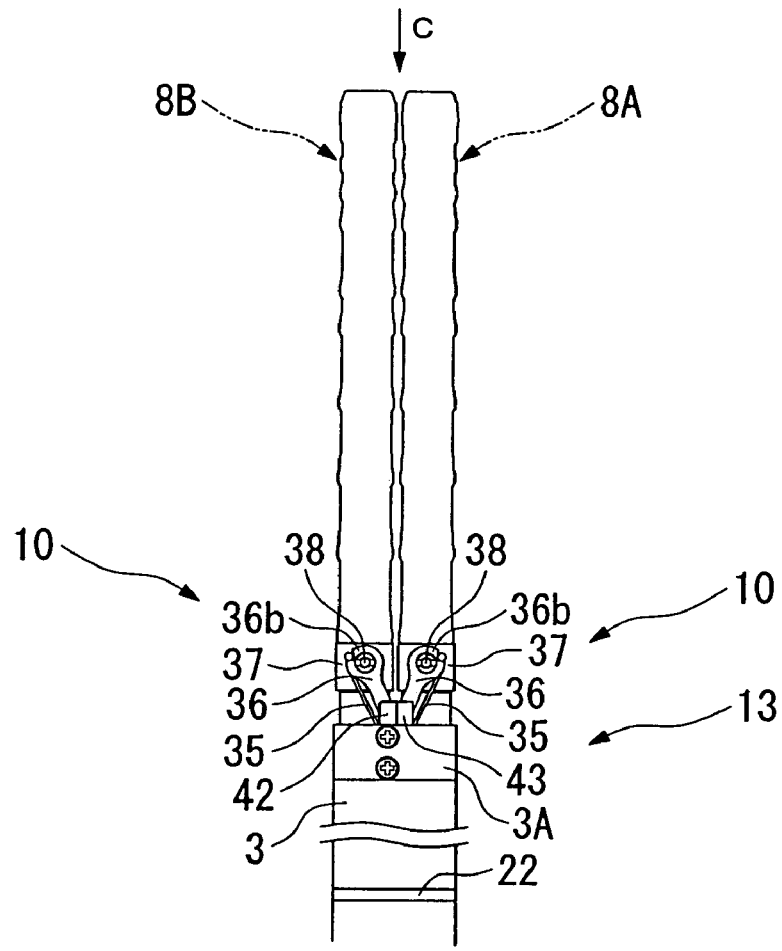
FIG. 7A is a plan view showing the starting state of the arm member of the medical treatment endoscope according to the first embodiment.
Figure 7B:
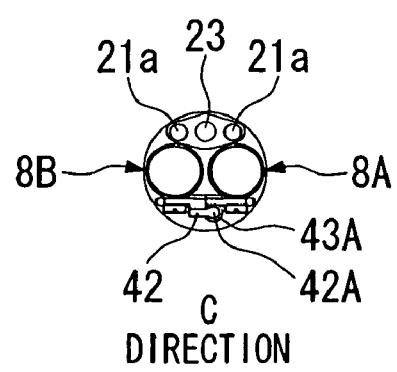
FIG. 7B is a view along the direction C in FIG. 7A.

A video cable 20, which is connected to a viewing device 12 which includes an image pick-up unit 11 and an objective lens (optical member for viewing) 23, and two light guides (illuminating members) 21A and 21B which emit illuminating light onto illuminating lenses (illuminating optical members) 21a, which are structural components of the illuminating members and are for lighting the object to be illuminated by forming the illuminating light bundles into a desired light bundle profile, are inserted into the first sheath 3 so as not to interfere with the second sheath 9A, the third sheath 9B and the various bending wires. A rigid sheath front end part 3A is disposed to the front end of the first sheath 3. Objective lens 23, and illuminating lenses 21a which are on either side of the objective lens so as to interpose the objective lens 23 therebetween, are disposed to the sheath front end part 3A. In other words, the illuminating members are disposed on either side of the viewing device. As shown in FIG. 7A, a plurality of markings 22, for understanding a length of the inserted portion when the endoscope is inserted into the patient, are provided at predetermined intervals along the surface of the first sheath 3 on the hand-held side thereof.

As shown in FIGS. 1, 2A, 2B, and 10, a gripping forceps 5 is provided with a forceps insertion part 25 that has a long narrow coil sheath 25a. A pair of forceps pieces 26A and 26B are disposed to the front end of the forceps insertion part 25. This pair of forceps pieces 26A and 26B is connected to a forceps manipulating wire 27, which is inserted into the coil sheath 25a to enable free advancing and retracting, via a forceps linking part 28 which converts the advancing/retracting operation of the forceps manipulating wire 27 into the opening/closing operation of the paired forceps pieces 26A and 26B. A forceps linking part 28 is disposed to a front end cover 29 which is attached to the coil sheath 25a.

As shown in FIGS. 2A and 2B, this gripping forceps 5 is fixed in place via a first connecting member 30A, a second connecting member 30B and a third connecting member 30C to the second arm member 8B to enable free rotation. The first connecting member 30A is tubular, with its inner peripheral surface fixed in place near the front end of the gripping forceps 5 by a screw, adhesive agent or the like. The second connecting member 30B is in the form of a short pipe, and is interposed between the bumper 15a of the front end part 15 and the first connecting member 30A. The third connecting member 30C is in the form of a short pipe, and is formed so that the base end projects inward in the radial direction. This third connecting member 30C engages with the front end part 15, and pushes the first connecting member 30A in the forward direction. As a result, the second connecting member 30B is pushed further forward then the first connecting member 30A, coming into contact with the bumper 15a of the front end part 15, thereby restricting movement of the gripping forceps 5 in the advancing or retracting direction. The gripping forceps 5 are attached in a freely rotating manner with respect to the instrument insertion channel 6. Note that the third connecting member 30C may also be attached to the front end part 15 by screwing, or by an adhesive agent or the like.

The gripping forceps 5 are provided with a forceps operating part (procedure operating part) 31. The forceps operating part 31 is provided with a forceps operating part main body 32 to which the coil sheath 25a is connected, and a forceps handle 33 to which forceps manipulating wire 27 is connected and which is disposed in a freely retracting and advancing manner with respect to the forceps operating part main body 32.

The open/close mechanisms 10 are respectively provided corresponding to the number of the first arm members 8A and the second arm members 8B. Note that since the structure is almost entirely the same, the following explanation will be directed to the open/close mechanism 10 of the first arm member 8A.

As shown in FIGS. 4 through 8B, the open/close mechanism 10 is provided with a bending opening/closing wire (open/close operating member) 35, which is capable of advancing and retracting with respect to the first sheath 3; a linking part 36 to which the end of the bending opening/closing wire 35 is connected, which converts the advancing/retracting operation of the bending opening/closing wire 35 into the opening/closing operation of the first arm member 8A with respect to the first sheath 3; and a support 37 which is in the form of a short pipe that is axially supported to enable rotation about linking part 36, or, alternatively, is connected to linking part 36 in a manner so as to prevent rotation. This short pipe-shaped support 37 is fixed in place along the bending part 7 of the arm member 8A. Note that it is also acceptable to fix this short pipe-shaped support 37 further toward the base end than the bending part 7. The linking part 36 is formed extending in the form of a long plate, and one end 36a is axially supported by a guide member 42 of the first sheath 3, explained below, to enable rotation. Note that in the case of the second arm member 8B, the one end 36a of the linking part 36 is axially supported by a sliding member 43, explained below, that can advance and retract along the central axis C1.

The support 37 is supported by the other end 36b of the linking part 36 via a support axis 38, to enable rotation thereof, or alternatively, is connected so that rotation is not possible. The other end 36b of the linking part 36 is formed in the shape of a disk centered about the position of attachment to the support axis 38, with bending opening/closing wires 35 supported by the periphery thereof. The bending opening/closing wires 35 are disposed inside the first sheath 3, inserted into respective bending opening/closing wire coils 41.

An advance/retract mechanism 13 is provided with a guide member 42 extending in the direction of the central axis C1 of the first sheath 3 and fixed in place to the first sheath 3, and a sliding member 43 that can be freely advanced and retracted with respect to the guide member 42. The guide member 42 is formed in the shape of a flat plate extending a predetermined length in one direction, and, with respect to the central axis C1 of the first sheath 3, is disposed at a position opposite where the light guides 21A and 21B and the video cable 20 are inserted (i.e., the area opposite where the light guides 21A and 21B and the video cable 20 are inserted, such that the second sheath 9A and the third sheath 9B are interposed therebetween). An engaging convexity 42A, approximately cylindrical in shape, is provided to one end in the width direction of the guide member 42 on the first arm member 8A side. The sliding member 43 is provided with a roughly C-shaped engaging concavity 43A that engages with the engaging convexity 42A to enable sliding, and a connector 43B that links the engaging concavity 43A and the first arm member 8A. The amount of movement of the sliding member 43 with respect to the guide member 42 is restricted to predetermined limits. Note that it is also acceptable to enable advancing and retracting of the second arm member 8B, rather than the first arm member 8A, using the same type of advance/retract mechanism.

Figure 9:
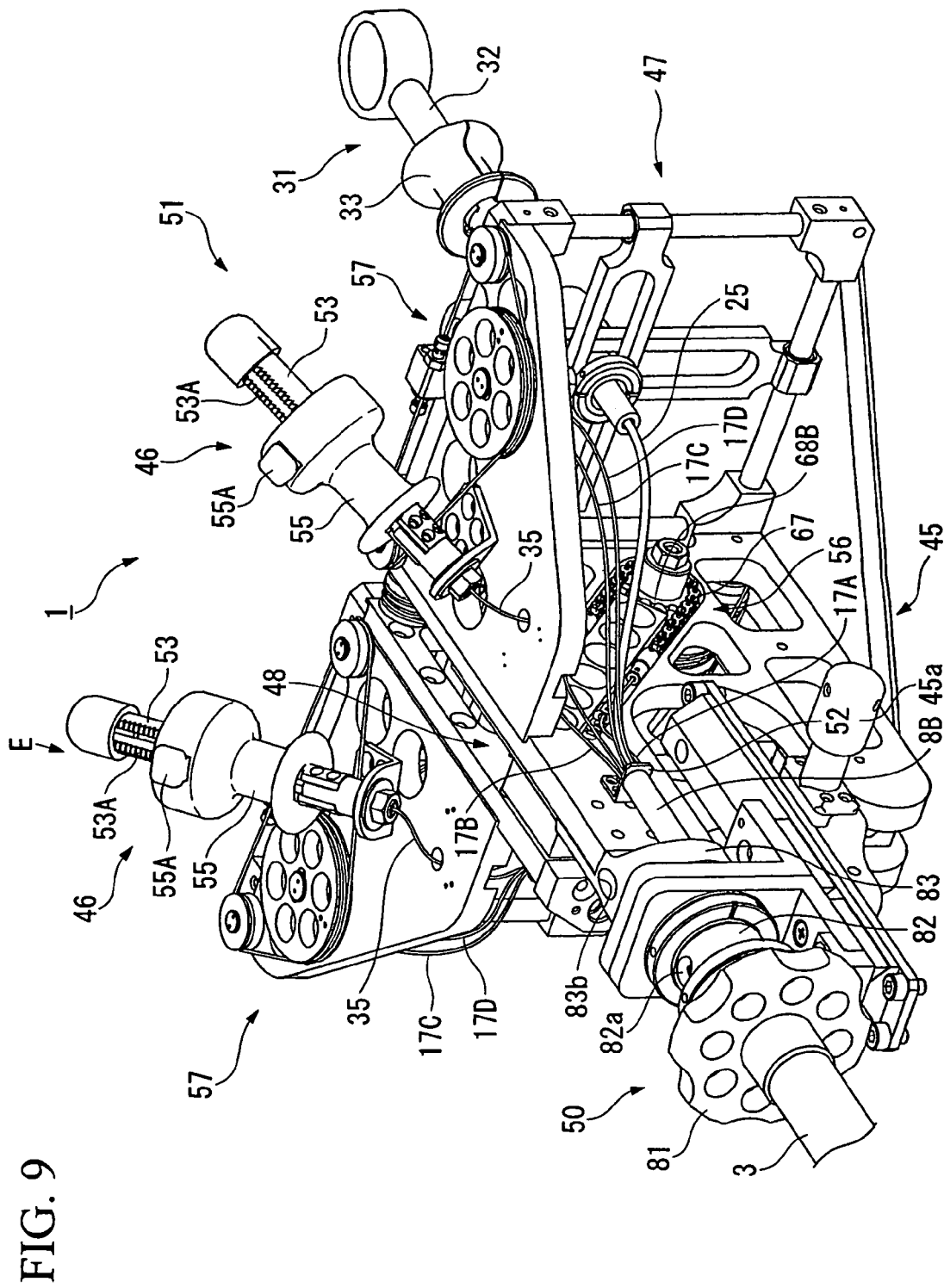
FIG. 9 is a perspective view showing the operating part of the medical treatment endoscope according to the first embodiment.
Figure 10:
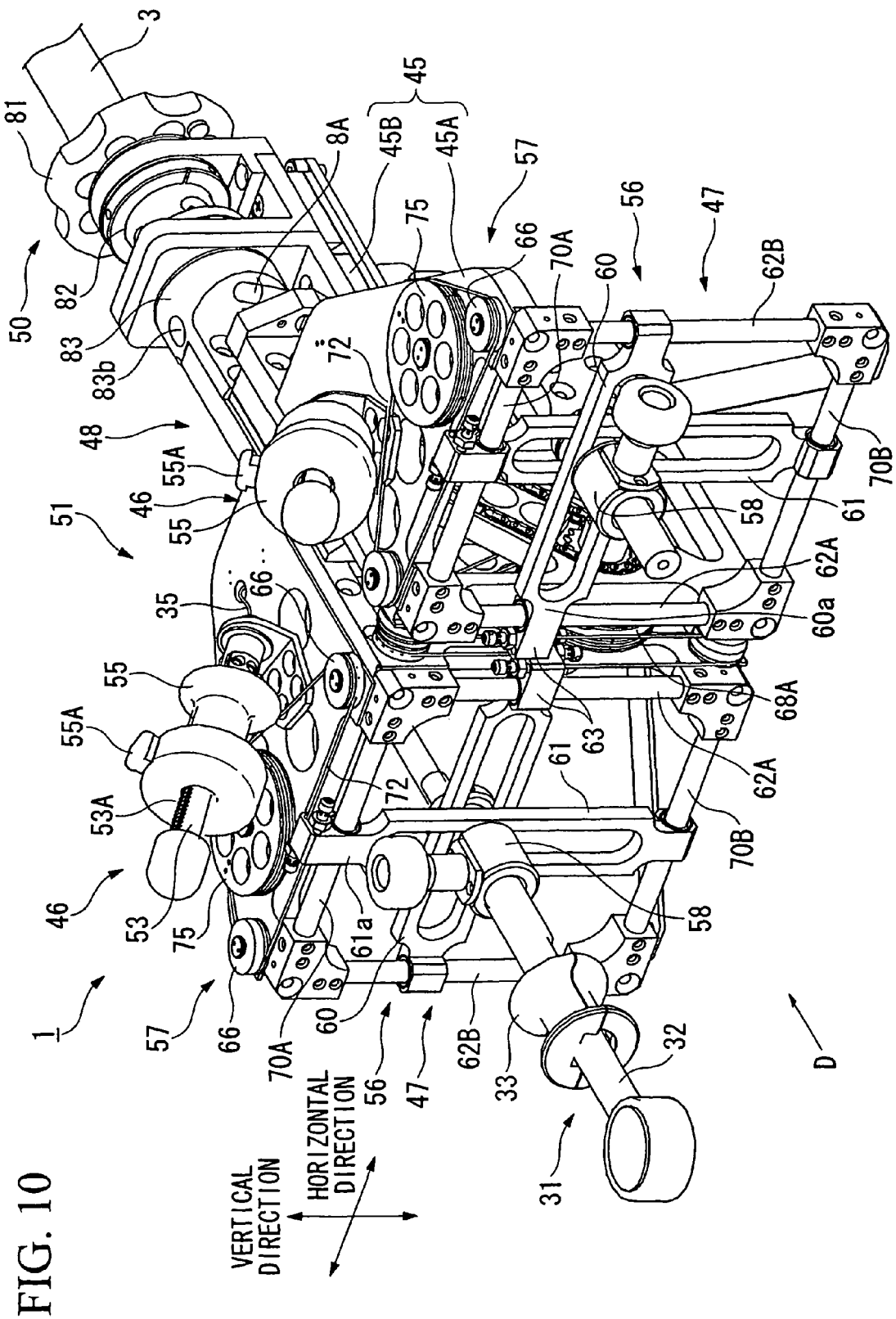
FIG. 10 is a view along the direction E in FIG. 9.
Figure 11:
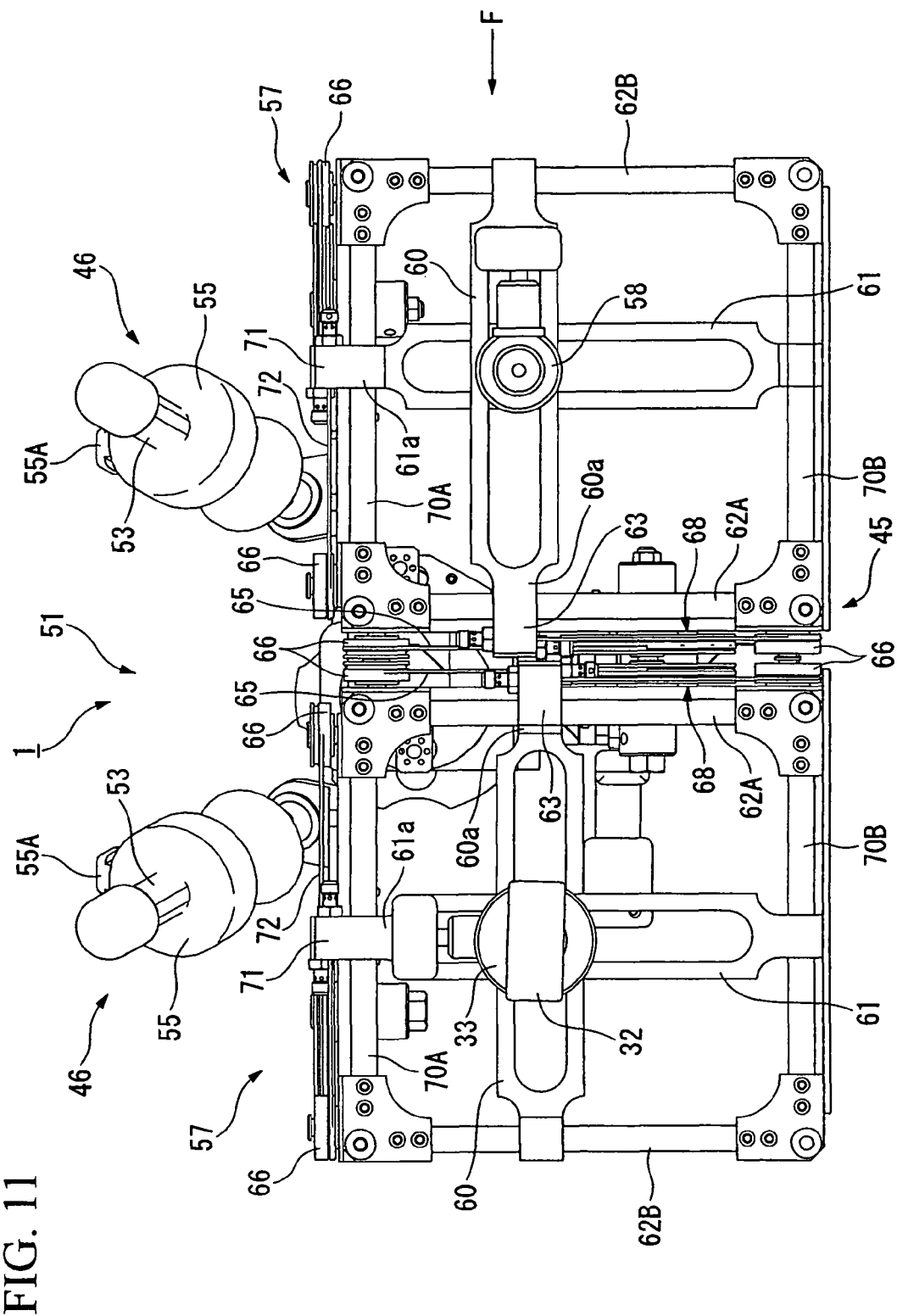
FIG. 11 is a view along the direction E in FIG. 10.
Figure 12:
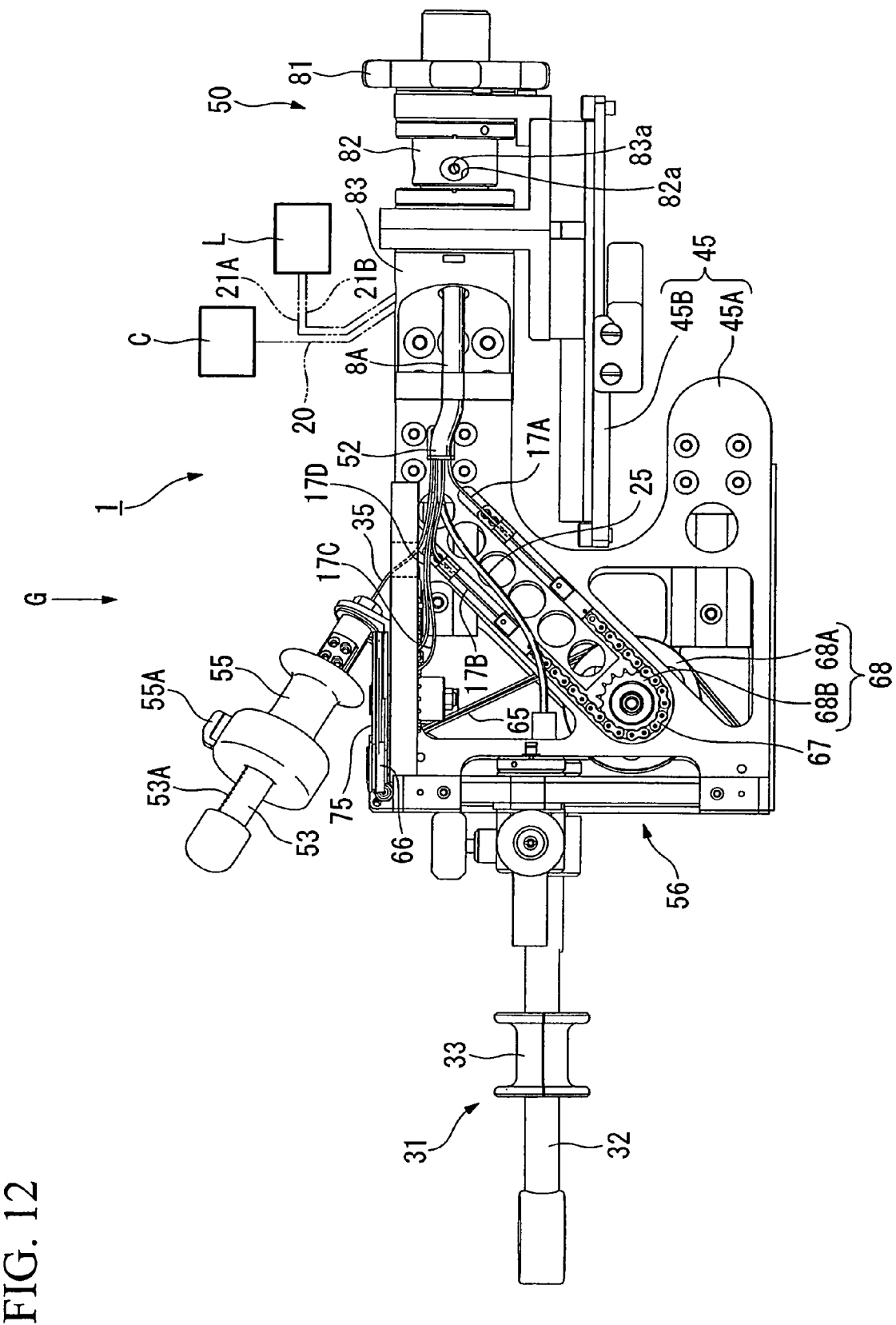
FIG. 12 is a view along the direction F in FIG. 11.
Figure 13:
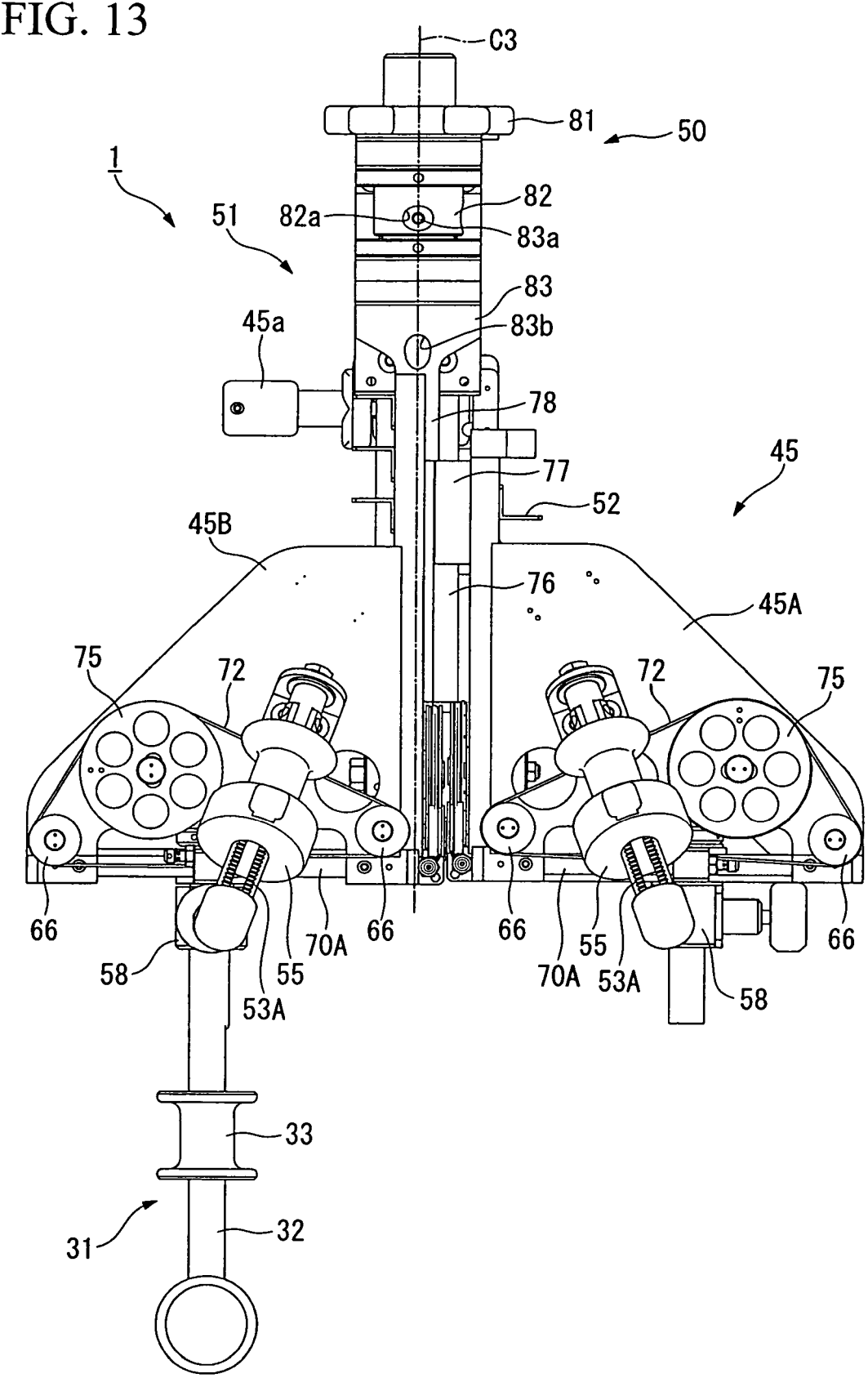
FIG. 13 is a view along the direction G in FIG. 12.

As shown in FIGS. 9 though 12, the medical treatment endoscope 1 is provided with an operating part 51 having a frame 45; an open/close operating part 46 that is connected to the base end of the bending opening/closing wire 35 of the open/close mechanism 10, for carrying out advancing and retracting manipulation of the bending opening/closing wire 35; a bending operating part 47, to which the forceps operating part 31 of the gripping forceps 5 can be attached, for advancing and retracting manipulation of the bending wires 17A, 17B, 17C, and 17D that are connected to the respective bending parts 7 of the first arm member 8A and the second arm member 8B by movement of the forceps operating part 31; an advance/retract operating part 48 for advancing and retracting the sliding member 43 of the advance/retract mechanism 13 with respect to the guide member 42; and a rotation operating part 50 for connecting the base end of the first sheath 3 to the frame 45 in a manner to enable rotation.

The frame 45 is provided with a moving frame 45A where the open/close operating part 46 and the bending operating part 47 of the arm member 8A are disposed; and a fixed frame 45B where the open/close operating part 46 and the bending operating part 47 of the arm member 8B, and the rotation operating part 50 of the first sheath 3, are disposed. Arm clamps 52 for supporting the first arm member 8A and the second arm member 8B projecting from the base end of the first sheath 3 farther toward the hand-held side are respectively disposed along the central axis C3 to moving frame 45A and fixed frame 45B. In addition to the first arm member 8A and the second arm member 8B, the light guides 21A and 21B and the video cable 20 project out from the base end of the first sheath 3, and are connected respectively to a light source device L and a controller C. A fixing screw 45a for connecting and fixing in place a scope holder 86, explained below, is disposed to the bottom of the fixed frame 45B. Note that with respect to fixing with the scope holder 86, it is also acceptable enable free sliding so that it is possible to adjust the position of the front end of the medical treatment endoscope 1 inside the body cavity by advancing and retracting the entire operating part.

The open/close operating part 46 is provided with an open/close operating part main body 53 and an open/close handle 55 to which the base end of the bending opening/closing wire 35 is connected and which can advance and retract with respect to the open/close handle main body 53. The open/close operating part main body 53 is respectively fixed in place to the fixed frame 45B and the moving frame 45A. A rack 53A is formed to the open/close operating part main body 53 for restricting movement toward the front end side when the open/close handle 55 is pulled toward the hand-held side. The advance of the open/close handle 55 with respect to the open/close operating part main body 53 is restricted as a result of engagement of this rack 53A with a gear, not shown in the figures, that is provided inside the open/close handle 55. In this restricted state, the above-mentioned gear can be moved away and released from the rack 53A by pressing a release button 55A that is provided to the open/close handle 55. When a starting state for the open/close mechanism 10 is defined as the state in which the first arm member 8A and the second arm member 8B are closed at a position along the direction of the central axis C1 of the first sheath 3, then, in this starting state, the open/close handle 55 is set so as to be positioned toward the front end of the open/close operating part main body 53.

The bending operating part 47 is provided with a vertical bending operating part 56 for moving bending part 7 in the vertical direction, for example; a horizontal bending operating part 57 for moving the bending part 7 is a direction perpendicular to the aforementioned, i.e., moving the bending part 7 in the horizontal direction, for example; and an attachment part 58 for attaching the forceps operating part main body 32 of the forceps operating part 31 in a manner so as to enable its rotation. The attachment part 58 is connected to enable movement in the respective directions inside the each of the frames at the area of intersection between a first movement restricting member 60, which is in the form of a rectangular frame provided for causing relative displacement of the attachment part 58 in the horizontal direction only, and a second movement restricting member 61, which is in the form of a rectangular frame disposed perpendicular to the first movement restricting member 60 and provided for causing relative displacement of the attachment part 58 in the vertical direction only. Note that bending operating parts 47 are disposed to each of the first arm member 8A and the second arm member 8B.

A vertical bending operating part 56 is provided with a pair of rod-shaped first bending guides 62A and 62B in which the longitudinal ends of the first movement restricting member 60 are engaged in a manner to enable sliding, in order to cause parallel displacement of the first movement restricting member 60 in the vertical direction; a first die part 63 that is connected to the end 60a of the first movement restricting member 60, and moves along the first bending guide 62A; a first belt member 65, in which both ends are connected to the first die part 63 so as to be in opposition to one another from the direction along the first bending guide 62A; two adjusting wheels 66 for adjusting the tension by winding the first belt member 65; a first chain belt 67 in which the bases of the bending wires 17A and 17B are connected at either end; and a first gear 68 having a large diameter part 68a in which the first chain belt 67 engages and a small diameter part 68b around which the first belt member 65 is wound.

A horizontal bending operating part 57 is provided with the same design as the vertical bending operating part 56. In other words, horizontal bending operating part 57 is equipped with a pair of rod-shaped second bending guides 70A and 70B in which the longitudinal ends of the second movement restricting member 61 are engaged in a manner to enable sliding, in order to cause parallel displacement of the second movement restricting member 61 in the horizontal direction; a second die part 71 that is connected to the end 61a of the second movement restricting member 61, and moves along the second bending guide 70A; a second belt member 72, in which both ends are connected with respect to the second die part 71 so as to be in opposition to one another from the direction along the second bending guide 70A; adjusting wheels 66 for adjusting the tension by winding the second belt member 72; a second chain belt, not shown in the figures, in which the bases of the bending wires 17C and 17D are connected at either end; and a second gear 75 in which the second chain belt engages and around which the second belt member 72 is wound.

The advance/retract operating part 48 is provided with a slide rail 76 for moving the moving frame 45A, to which the open/close operating part 46 and the bending operating part 47 connected to the arm member 8A are disposed, with respect to the fixed frame 45B; and a base 77 which is disposed to the moving frame 45A and engages in a sliding manner with the slide rail 76. An advance/retract restricting member 78 is disposed to the front end side of the slide rail 76. The amount of sliding of the moving frame 45A is restricted to a predetermined range as a result of the base 77 coming into contact with this advance/retract restricting member 78. This advance/retract restricting member 78 is positioned at a predetermined location so that the sliding member 43 of the advance/retract mechanism 13 does not come free from the guide member 42.

The rotation operating part 50 is disposed further toward the front end side of the frame 45 than the arm clamp 52, and is provided with a sheath connector 82, to which a rotation knob 81 is disposed and the base end of the first sheath 3 is connected; and a rotation support 83 for supporting the sheath connector 82 in a manner to enable rotation. A screw hole 83a is formed in the rotation support 83, and a through hole 82a is formed in the sheath connector 82. The rotation of the sheath connector 82 with respect to the rotation support 83 is restricted as a result of the engagement of a stopping screw or the like at the position where the screw hole 83a and the through hole 82a are overlapped. The amount of rotation is preferably on the order of 180 degrees to either side. Note that a through hole 83b is disposed to the rotation support 83 for insertion of the light guides 21A and 21B and the video cable 20.

Next, the operation of the embodiments of the present invention will be explained.

Figure 5A:
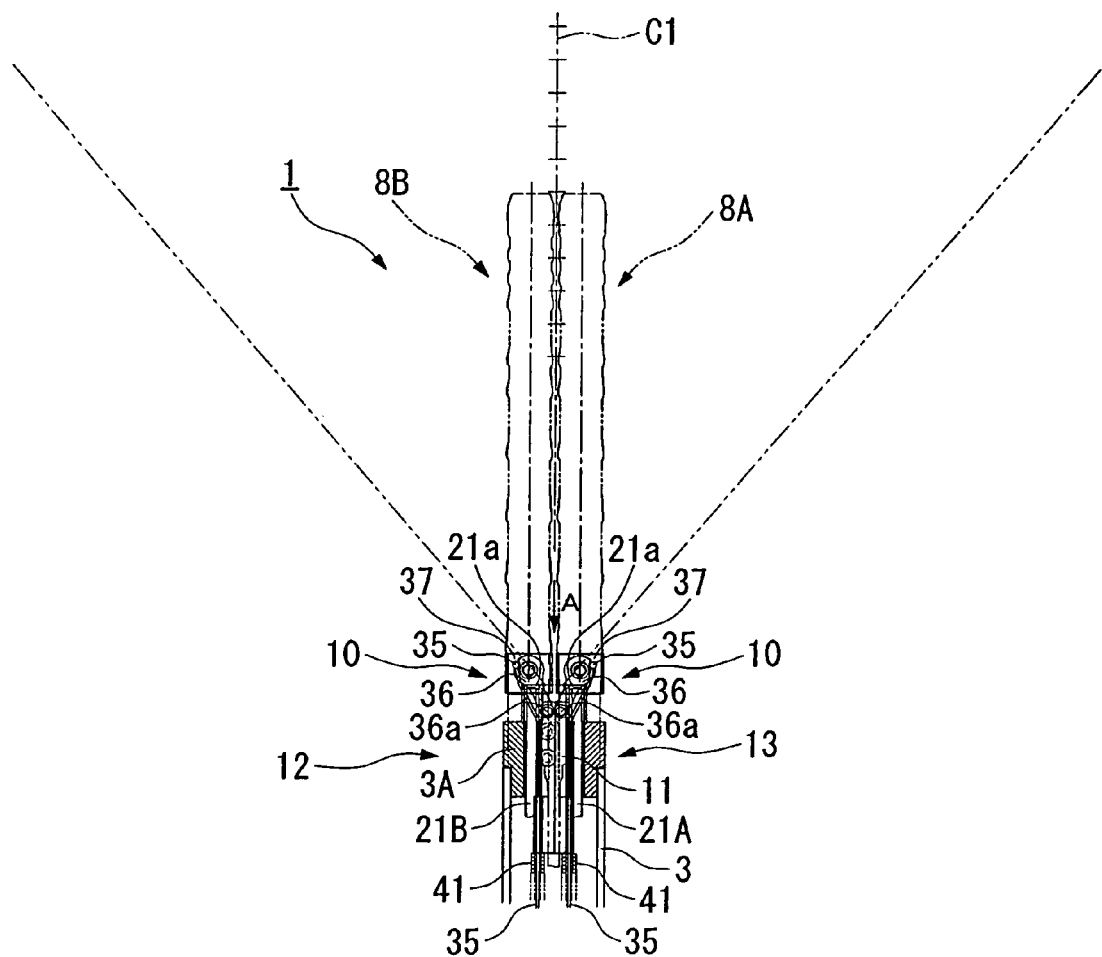
FIG. 5A is a perspective view showing the starting state of the arm member of the medical treatment endoscope according to the first embodiment.
Figure 5B:
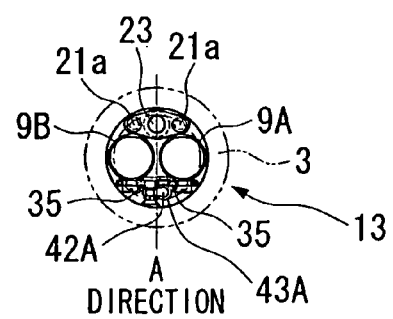
FIG. 5B is a view along the direction A in FIG. 5A.
Figure 6A:
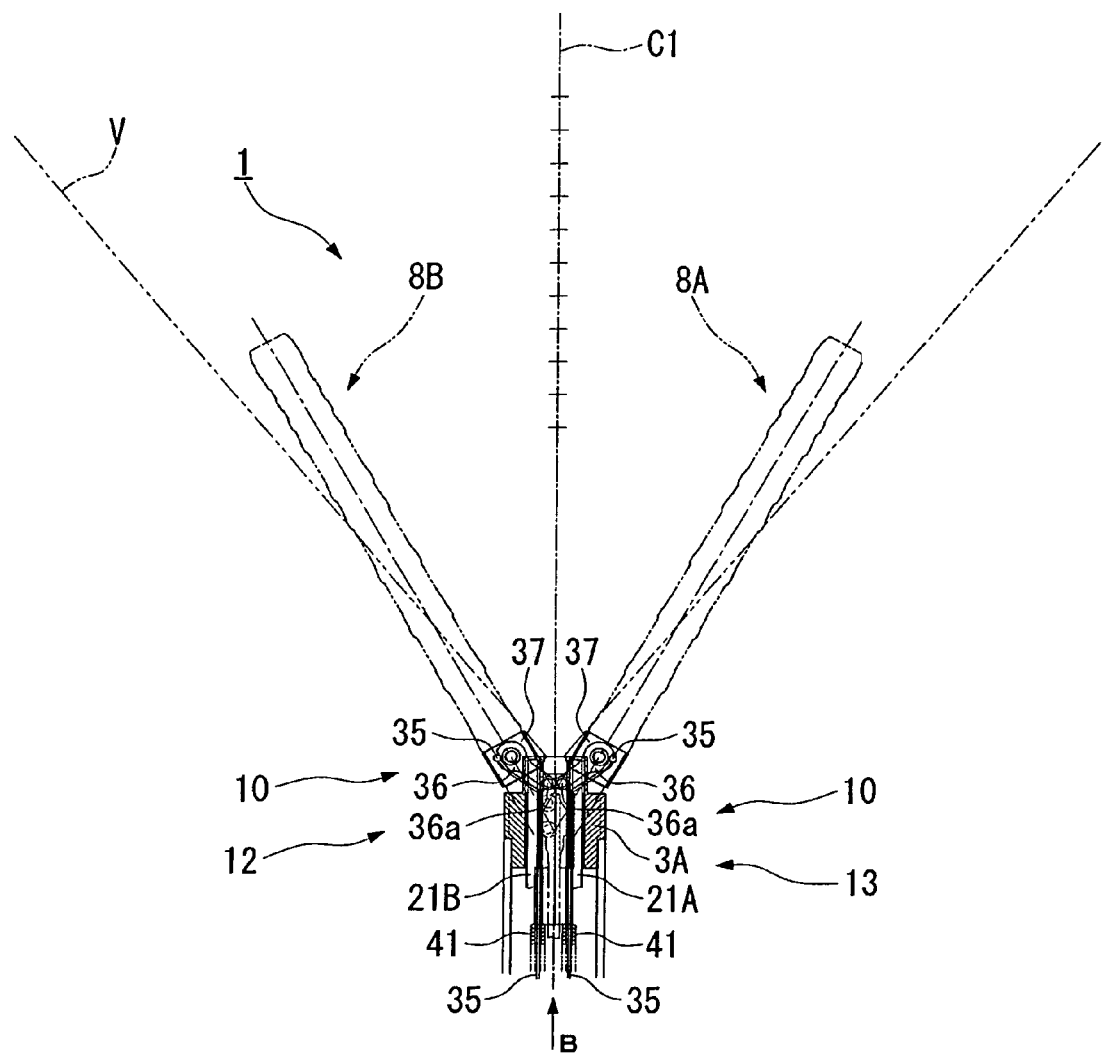
FIG. 6A is a perspective view of the front end showing the arm member of the medical treatment endoscope according to the first embodiment in the open state.
Figure 6B:
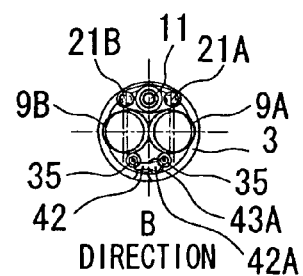
FIG. 6B is a view along the direction B in FIG. 6A.
Figure 8A:
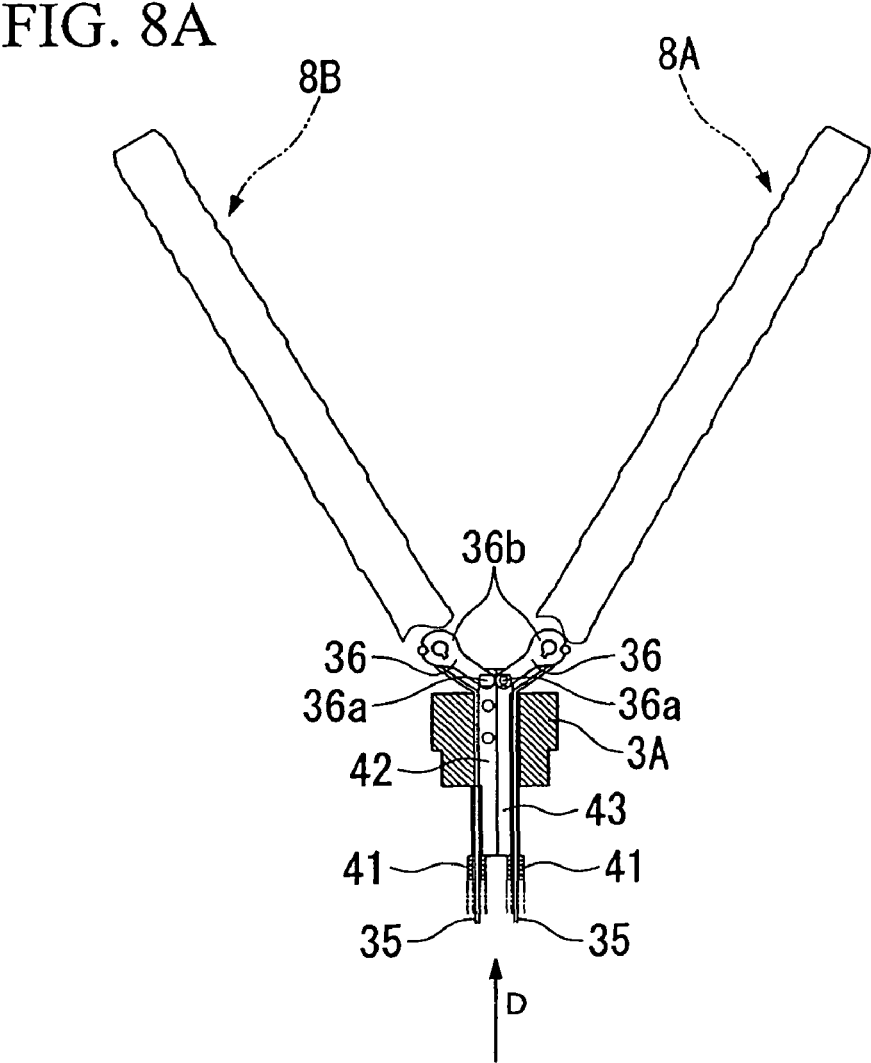
FIG. 8A is a plan view showing the open/close mechanism when the arm member of the medical treatment endoscope according to the first embodiment is in the open state.
Figure 8B:
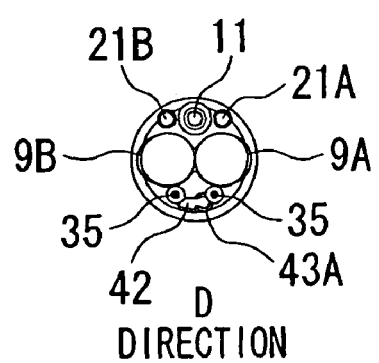
FIG. 8B is a view along the direction D in FIG. 8A.

When opening the first arm member 8A and the second arm member 8B with respect to the first sheath 3 from the starting state shown in FIGS. 5A and 7A, the open/close handle 55 is slide with respect to the open/close operating part main body 53 a predetermined distance toward the hand-held side. The bending opening/closing wire 35 is thus retracted with respect to the first sheath 3 toward the hand-held side. Accompanying this, the other end 36b of the linking part 36 receives a rotational torque toward the base end side of the first sheath 3. The other end 36b side of the linking part 36 is rotated about the one end 36a by a predetermined angle in the direction away from the central axis C1 of the first sheath 3. As shown in FIGS. 6A and 8A, the support 37 rotates with respect to first sheath 3, and opens. In this case, the position of the open/close handle 55 is fixed in place by the rack 53A of open/close operating part main body 53, and the position of the bending opening/closing wire 35 is thus fixed in place with respect to the first sheath 3.

When closing the first arm member 8A and the second arm member 8B with respect to the first sheath 3, the open/close handle 55 is advanced forward with respect to the open/close operating part main body 53, while pressing on the release button 55A of the open/close handle 55. The bending opening/closing wire 35 is advanced forward with respect to the first sheath 3 at this time. Accompanying this, the rotational torque applied on the linking part 36 is released, and the other end 36b of the linking part 36 is rotated about the one end 36a of the linking part 36 in a direction toward the central axis C1 of the first sheath 3. As a result, the support 37 rotates with respect to the first sheath 3 and closes, i.e., resumes the starting state.

Figure 14:
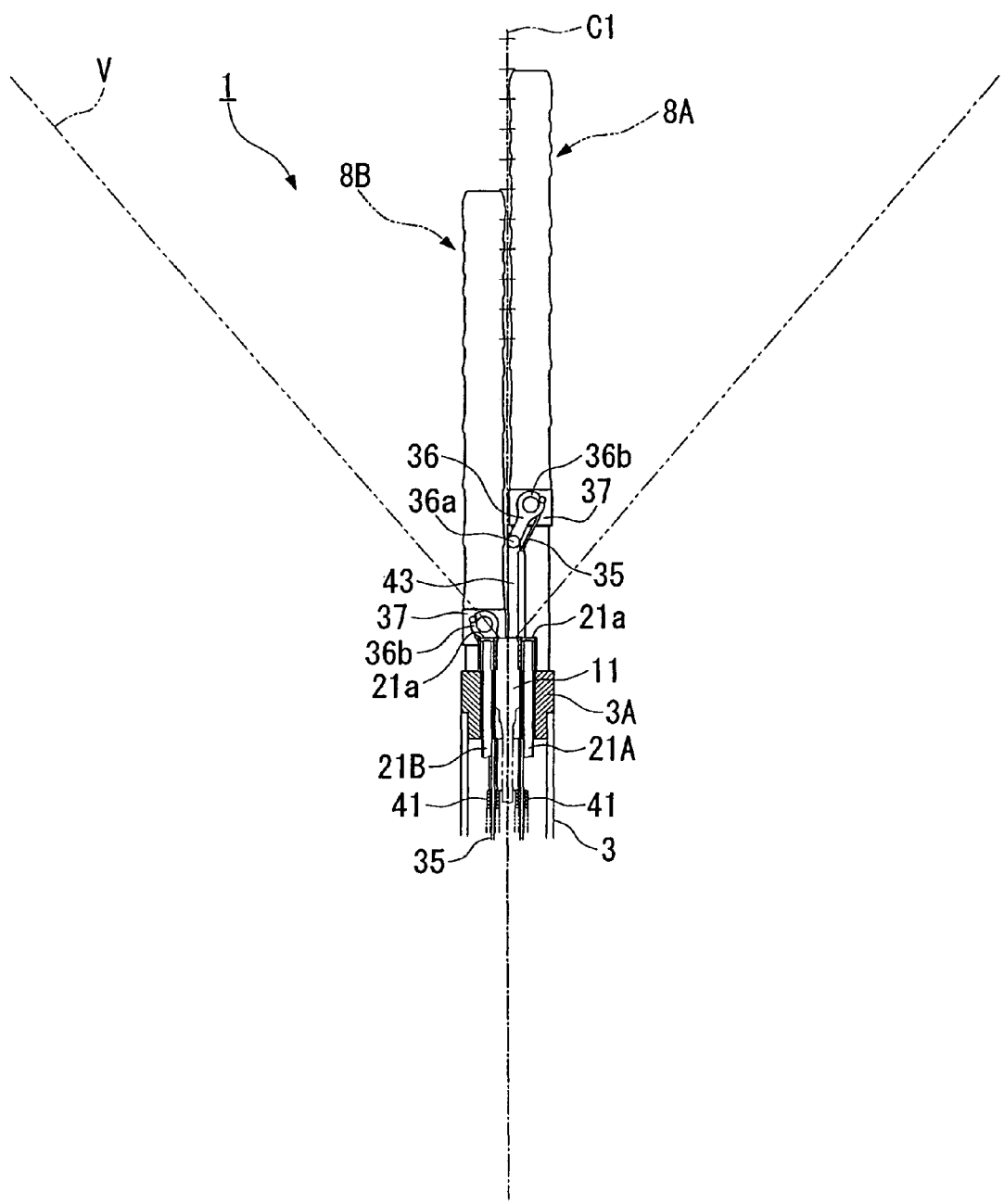
FIG. 14 is a view showing the state in which one of the arm members of the medical treatment endoscope according to the first embodiment has been moved forward with respect to the sheath.
Figure 15:
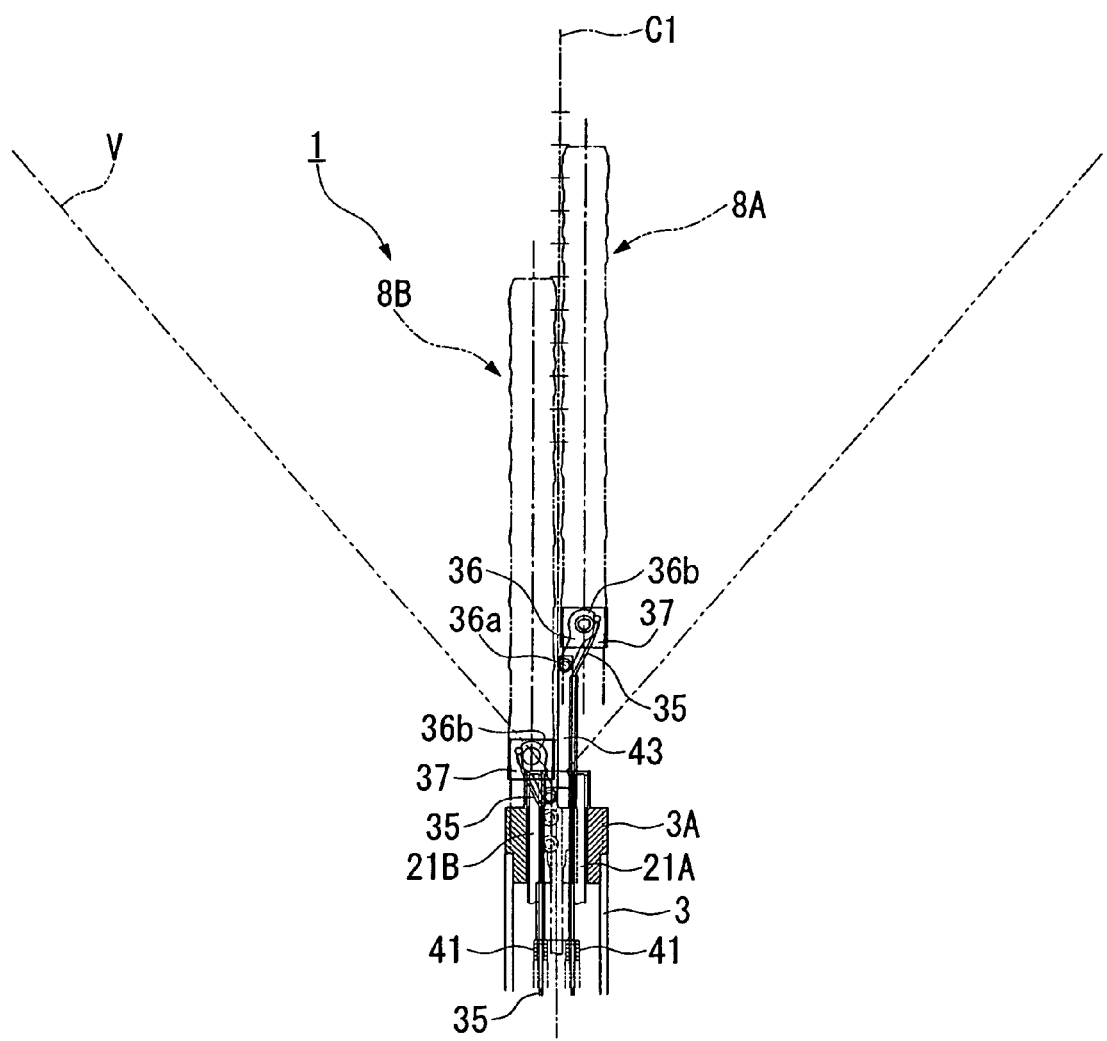
FIG. 15 is a partial perspective view of FIG. 14.
Figure 16:
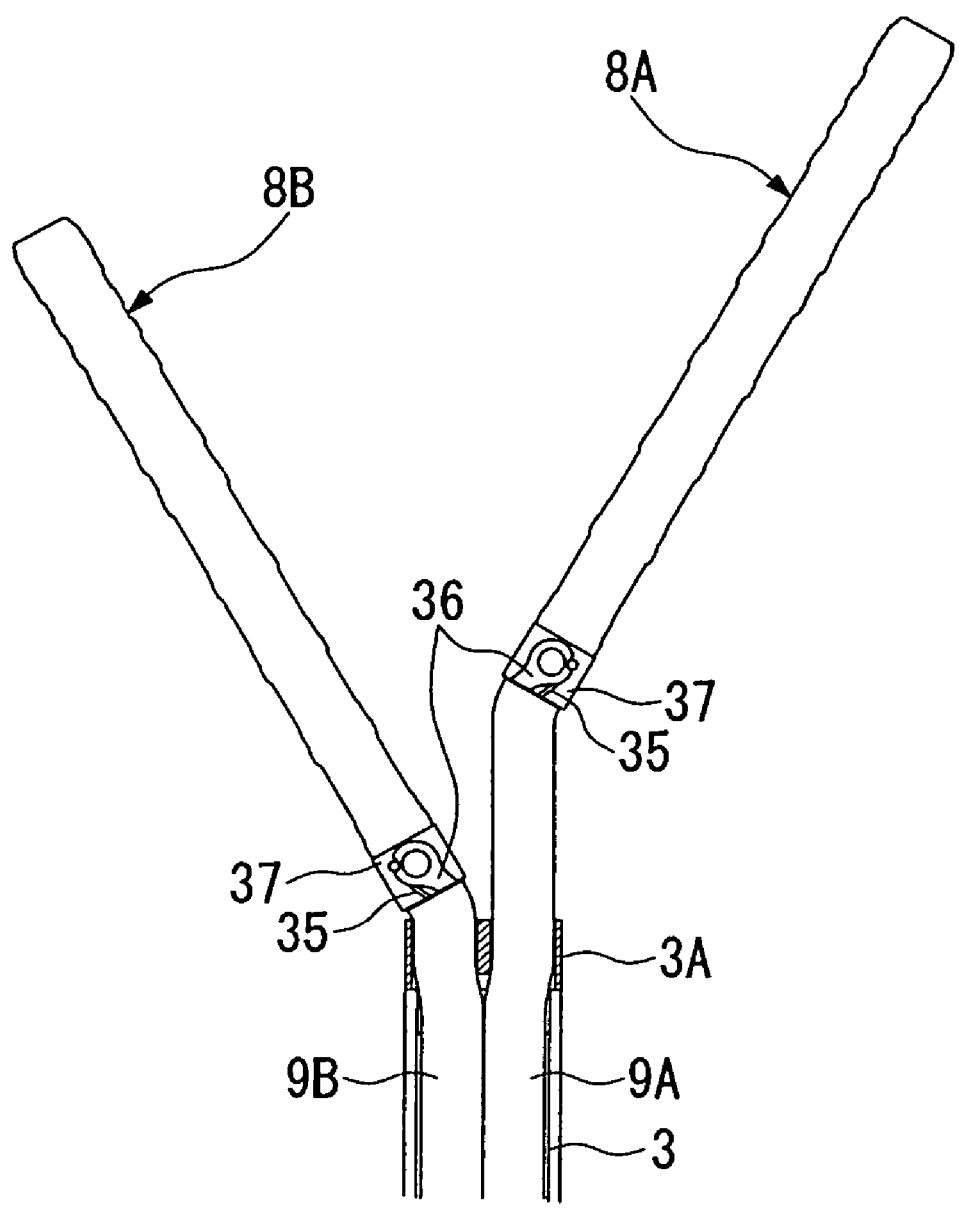
FIG. 16 is a view showing the state in which one of the arm members of the medical treatment endoscope according to the first embodiment has been moved forward with respect to the sheath, and further opened.
Figure 17:
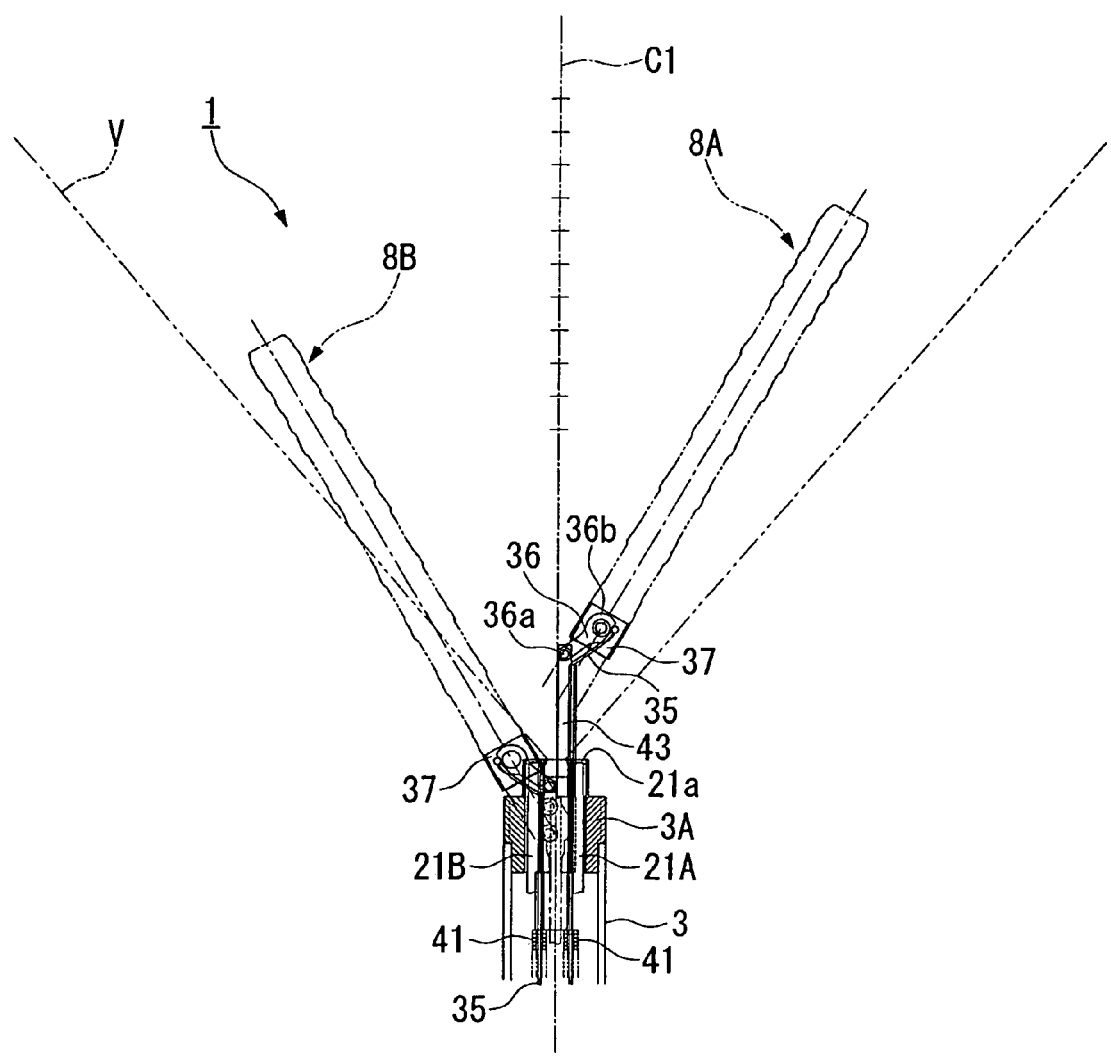
FIG. 17 is a partial perspective view of FIG. 16.

The moving frame 45A of the operating part 51 is advanced with respect to the fixed frame 45B, from the starting state shown in FIGS. 5A and 7A, when moving the first arm member 8A further toward the front end side of the first sheath 3. At this time, the base 77 advances along the slide rail 76, while the sliding member 43 of the open/close mechanism 10 moves forward with respect to the guide member 42. In this case, the entirety of the moving frame 45A moves, so that both the bending operating part 47 and the open/close operating part 46 move. Accordingly, there is no change in the open/close state and the bending state of the first arm member 8A. In this way, as shown in FIGS. 14 and 15, the first arm member 8A enters a state where it is advanced with respect to the first sheath 3.

In contrast, the moving frame 45A of the operating part 51 is retracted with respect to the fixed frame 45B when moving the first arm member 8A toward the hand-held side of the first sheath 3. At this time, the base 77 is retracted along the slide rail 76, while the sliding member 43 of the open/close mechanism 10 is retracted with respect to the guide member 42. As a result, the first arm member 8A is again disposed at the starting state position.

When bending the first arm member 8A and the second arm member 8B in the vertical direction, the vertical bending operating part 56 is manipulated. In other words, the forceps operating part 31 which is attached to the attachment part 58 is gripped and moved in the vertical direction. In this case, the attachment part 58 moves vertically with the limits of the second movement restricting member 61, while at the same time, the first movement restricting member 60 moves together with the attachment part 58 along the paired first bending guides 62A and 62B. Here, the first die part 63 also moves in the vertical direction, so that the first belt member 65 moves accompanying this, and the first gear 68 is rotated in either direction. At this time, the first chain belt 67 is rotated in either direction, and, accompanying this, one of the bending wires 17A and 17B is advanced with respect to the first sheath 3, while the other is retracted. In this way, the joint wheels 16 of the bending part 7 are inclined accompanying the movement of the bending wires 17A and 17B, and bend vertically.

In contrast, when bending the first arm member 8A and the second arm member 8B in the horizontal direction, the horizontal bending operating part 57 is manipulated. In other words, the forceps operating part 31 which is attached to the attachment part 58 is gripped and moved in the horizontal direction. In this case, the attachment part 58 moves horizontally within the limits of the first movement restricting member 60, while at the same time, the second movement restricting member 61 moves together with the attachment part 58 along the paired second bending guides 70A and 70B. Here, the second die part 71 also moves in the horizontal direction, so that the second belt member 72 moves accompanying this, and the second gear 75 is rotated in either direction. At this time, the second chain belt 73 is rotated in either direction, and, accompanying this, one of the bending wires 17C and 17D is advanced with respect to the first sheath 3, while the other is retracted. In this way, the joint wheels 16 of the bending part 7 are inclined accompanying the movement of the bending wires 17C and 17D, and bend horizontally.

When rotating the first sheath 3 with respect to the operating part 51, the rotation knob 81 of the rotation operating part 50 is gripped and rotated in the desired direction. As a result, the sheath connector 82 rotates relative to the rotation support 83, causing the first sheath 3 to rotate in the desired direction relative to operating part 51.

Figure 18:
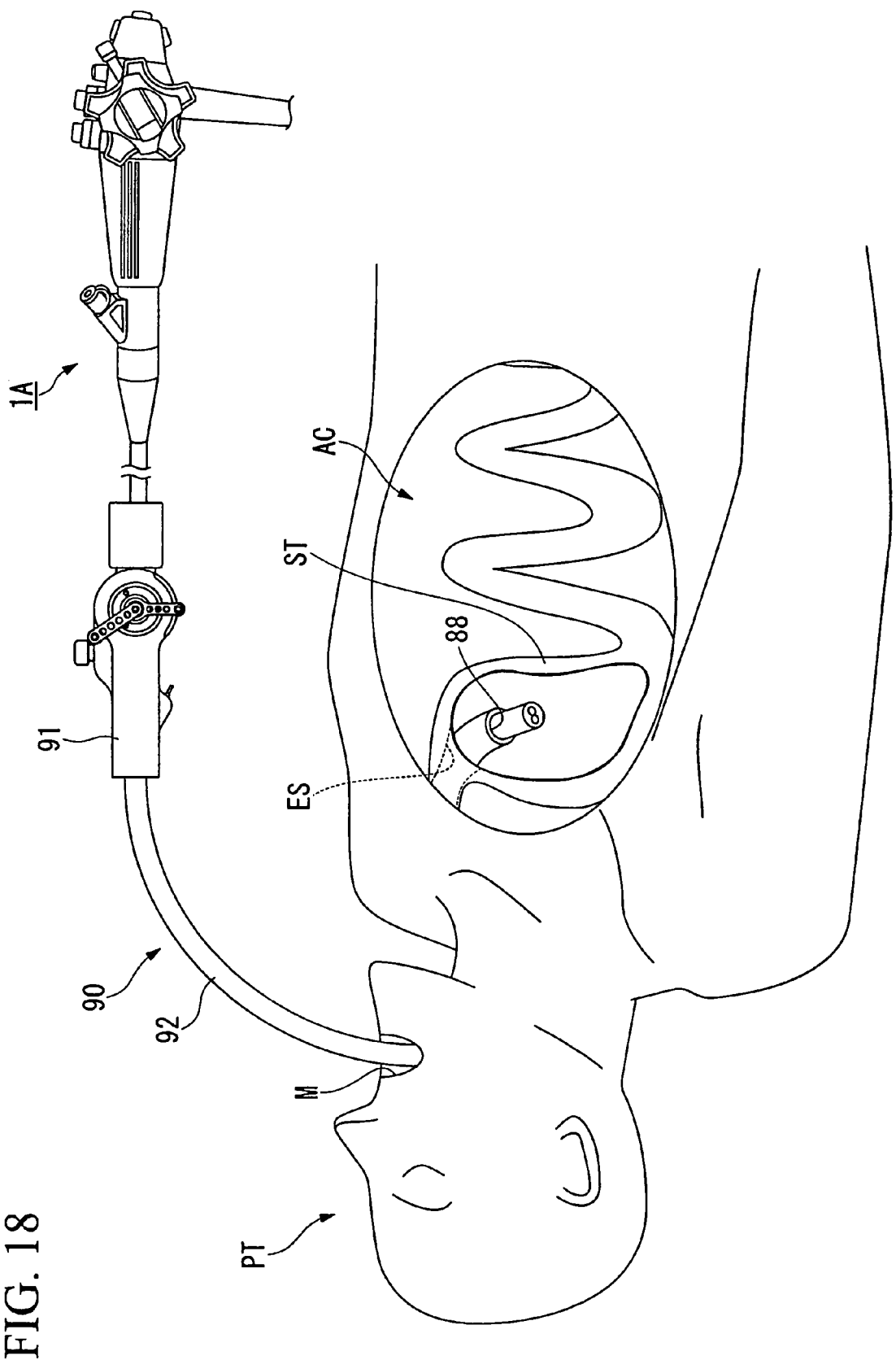
FIG. 18 is a view for explaining the state in which the endoscope has been inserted into an over-tube, and then inserted into the stomach, in an operative procedure using the medical treatment endoscope according to the first embodiment.

Next, an explanation will be made with reference to FIGS. 18 through 20 of an operative procedure performed via a natural orifice using the medical treatment endoscope 1. Note that the following explanation concerns the technique of inserting a medical treatment endoscope 1 from the mouth M of a patient PT into the stomach ST, opening a hole in the wall of the stomach, and then carrying out a procedure by inserting the first sheath 3 of the medial procedure endoscope 1 into the abdominal cavity AC. In the case of the present embodiments, a predetermined procedure is performed by inserting a high frequency knife 85 into the first arm member 8A, and a gripping forceps 85 into the second arm member 8B.

The patient PT is placed on his/her back, and a typical endoscope IA is introduced into the open-ended lumen 88 of an over-tube 90 from the base end 91 of the over-tube 90. This open-ended lumen 88 extends along the axial direction of the over-tube 90. The over-tube 90 is then inserted from the mouth M of the patient PT into the esophagus ES, and positioned in the stomach ST as shown in FIG. 18. Next, the stomach ST is inflated by relaying air into it, after which an opening SO is formed in the stomach wall by excision. The insertion part 92 of the over-tube 90 and the endoscope 1A are introduced into the abdominal cavity AC via the opening SO. Next, the endoscope 1A is withdrawn from the over-tube 90, and the first sheath 3 of the medical treatment endoscope 1 is inserted in its place into the lumen 88 of the over-tube 90, so as to project out from the front end of the over-tube 90.

As an example here, the case will be explained where a high-frequency knife 85 is inserted into the second sheath 9A and the first arm member 8A. First, the high-frequency knife 85 is inserted into the instrument insertion channel 6, and the front end of the high-frequency knife 85 comes into contact with the bumper 15a that is provided to the front end part 15 of the first arm member 9A. The front end of the high-frequency knife 85 is urged toward the bumper 15a by pushing the high-frequency knife 85 further in from the base end side, so that the knife operating part, not shown, of the high-frequency knife attaches into the attachment part 58 of the operating part 51. In this way, advancing and retracting of the high-frequency knife 85 with respect to the first arm member 9A is restricted. Note that the high-frequency knife 85 is supported to enable free rotation with respect to the first arm member 9A and the operating part 51.

Figure 19:
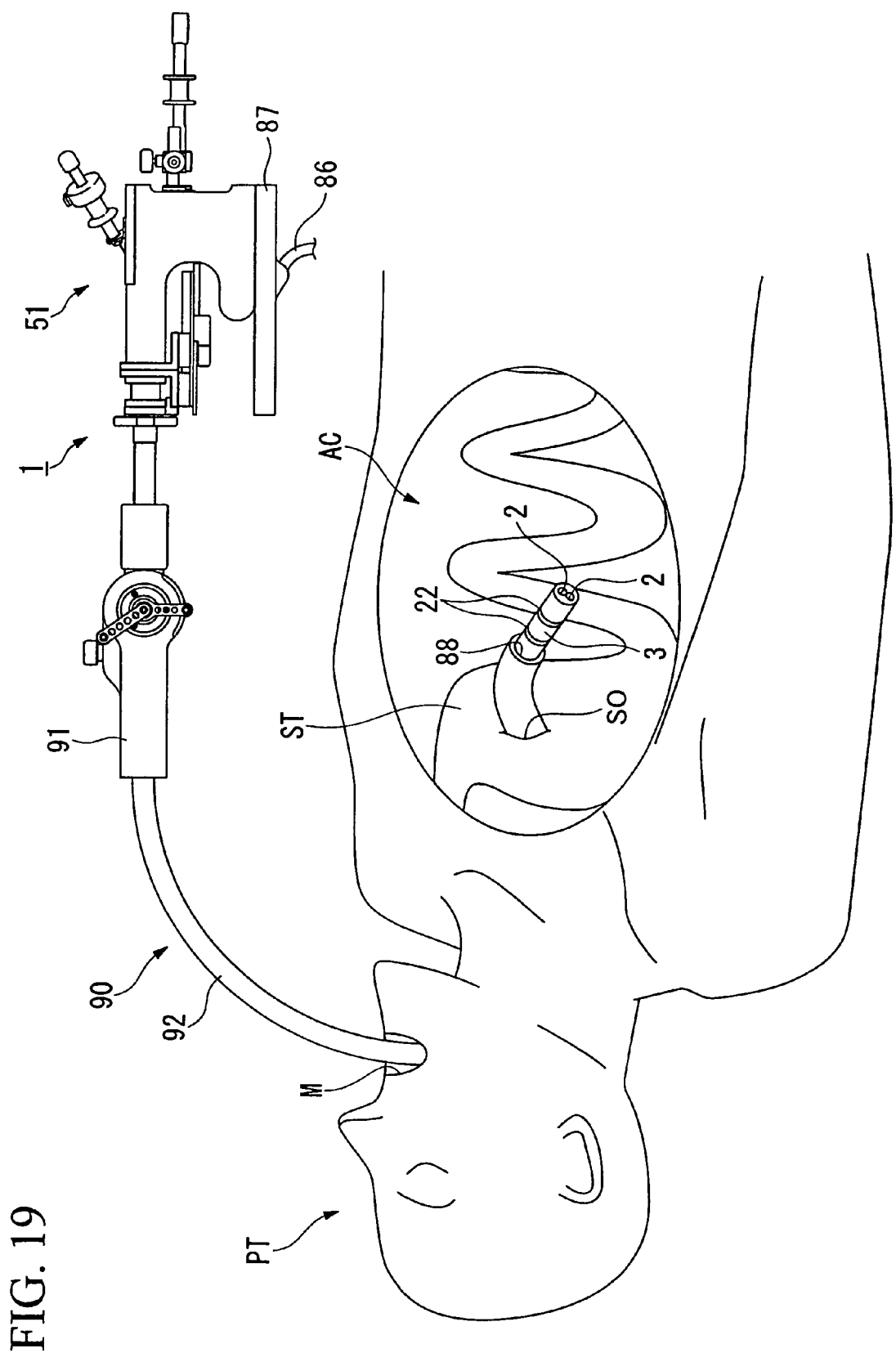
FIG. 19 is a view for explaining the state in which the endoscope has been inserted into an over-tube, and then inserted from the stomach into the abdominal cavity, in an operative procedure using the medical treatment endoscope according to the first embodiment.

As shown in FIG. 19, the operating part 51 of the medical treatment endoscope 1 is mounted in a manner to enable sliding to a mount 87 that is disposed to a scope holder 86 which is attached to a bed not shown in the figures.

Figure 20:
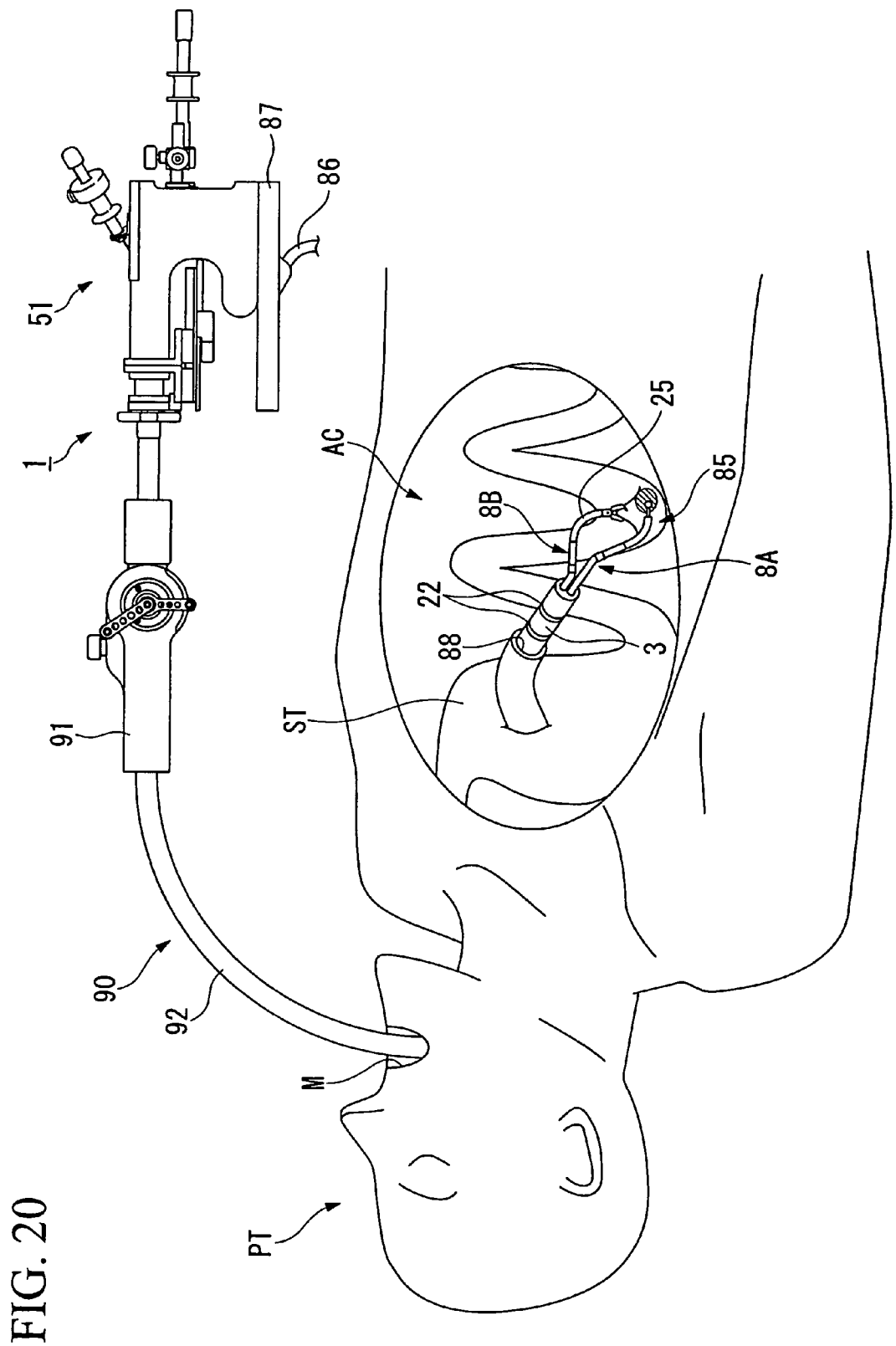
FIG. 20 is a view for explaining the state in which the procedure is carried out inside the abdominal cavity, in an operative procedure using the medical treatment endoscope according to the first embodiment.

After positioning, the operations of opening/closing, bending, and advancing/retracting of the first arm member 8A and the second arm member 8B are carried out according to the desired procedures, to perform a predetermined procedure, as shown in FIG. 20. After the procedure is carried out, the medical treatment endoscope 1 is withdrawn back into the stomach ST from the opening SO in the stomach wall, and then removed from the mouth M of the patient PT.

After suturing closed the opening SO in the stomach wall, the over-tube 90 and the medical treatment endoscope 1 are withdrawn from the patient, the pressure applied in the abdominal cavity AC is released and the procedure is terminated.

According to the medical treatment endoscope 1, the open/close mechanism 10 can be used to move the central axis C1 of the first arm member 8A and the second arm member 8B, which are respectively inserted into the first lumen 2 of the first sheath 3, away from the central axis C1 of the first sheath 3, further bending the bending part 7 of the first arm member 8A and the second arm member 8B. As a result, even if an instrument device such as gripping forceps 5 is inserted into the instrument insertion channel 6, the hand-held side of the first arm member 8A and the second arm member 8B bend with respect to the front end side of the first sheath 3. Thus, the inclination of the instrument device can be deviated from the line of vision V of the image pick-up unit 11 that is disposed to the sheath front end part 3A of the first sheath 3. Accordingly, it is possible to visually confirm the front end side of the first arm member 8A and the second arm member 8B with sufficient confirmation of the line of vision V of the image pick-up unit 11. As a result, the medical procedure can be carried out safely and assuredly.

In this case, the axial force generated by advancing and retracting the bending opening/closing wire 35 with respect to the first sheath 3 can be converted through the linking part 36 of the open/close mechanism 10 into the force for opening and closing the first arm member 8A and the second arm member 8B. As a result, the first arm member 8A and the second arm member 8B can be opened or closed with respect to the central axis C1 of the first sheath 3. In particular, when opening the first arm member 8A and the second arm member 8B, the bending opening/closing wire 35 is pulled toward the hand-held side. Accordingly, it is possible to adjust the transmission of force to the bending part 7, and to finely adjust the opening angle of the first sheath 3 with respect to the central axis C1. In addition, in the case where it has been designed that the first arm member 8A and the second arm member 8B will have a suitable angle of opening with respect to the central axis C1 by means of at once pulling the open/close handle 55 toward the hand-held side until it comes into contract with the open/close operating part main body 53, it is possible to simplify the open/close operation of the first arm member 8A and the second arm member 8B.

In addition, it is possible to operate the open/close mechanism 10 by operating the open/close operating part 46 of the operating part 51 to advance and retract the bending opening/closing wire 35 with respect to the first sheath 3. In addition, by performing operations with the forceps operating part 31 for the gripping forceps 5 in a state of attachment to the bending operating part 47, it is possible to carry out not only the opening/closing operation of the pair of forceps pieces 26A and 26B of the gripping forceps 5, but also carry out the bending operation of the bending part 7, thus facilitating the procedure.

Furthermore, by sliding the moving frame 45A with respect to the fixed frame 45B in the advance/retract operating part 48, it is possible to carry out the advance/retract operation of the first arm member 8A and the second arm member 8B with respect to the first sheath 3 by advancing or retracting the sliding member 43 with respect to the guide member 42. Accordingly, the treatment scope of the gripping forceps 5 with respect to the first sheath 3 can be expanded.

Furthermore, by rotating the rotation knob 81 of rotation operating part 50, the first sheath 3 can be rotated along with the first arm member 8A and the second arm member 8B from the base end side of the first sheath 3, and the opening/closing direction of the first arm member 8A and the second arm member 8B with respect to the first sheath 3 can be changed. Note that when it is desired to rotate a single instrument, then rotation to the desired state can be achieved by rotating the forceps operating part 31 with respect to the attachment part 58.

Because it is possible to use the support 37 of the open/close mechanism to support the first arm member 8A and the second arm member 8B farther toward the base end side than the bending part 7, the entirety of the bending part 7 can be used in the bending action, regardless of whether performing the open/close operation or the bending operation. Thus, the degree of freedom of the arm can be improved. Conversely, when the support 37 is provided along the bending part 7, the degree of freedom of each of the arm members is decreased, however, greater force can be delivered. In addition, by manipulating the bending part 7 of the first arm member 8A and the second arm member 8B which has a larger diameter than the diameter of the instrument insertion channel 6, the instrument can be more easily bent, and the procedure performed, than in the case where inserting a single instrument having bending capabilities through the instrument insertion channel 6 and then bending the instrument.

In addition, since the bending part 7 is employed only for bending an instrument such as gripping forceps 5 or the like, it is possible to achieve greater bending, and output greater force, as compared to a design that requires bending of a plurality of objects such as instruments, video cables (image guides in optical endoscopes), light guides and the like, such as seen in conventional endoscopes.

Second Embodiment

A second embodiment of the present invention will now be explained with reference to the figures.

The second embodiment differs from the first embodiment with respect to the point that both the first arm member 8A and the second arm member 8B of the medical treatment endoscope 100 according to this embodiment are designed to advance and retract with respect a sheath 101.

Figure 21:
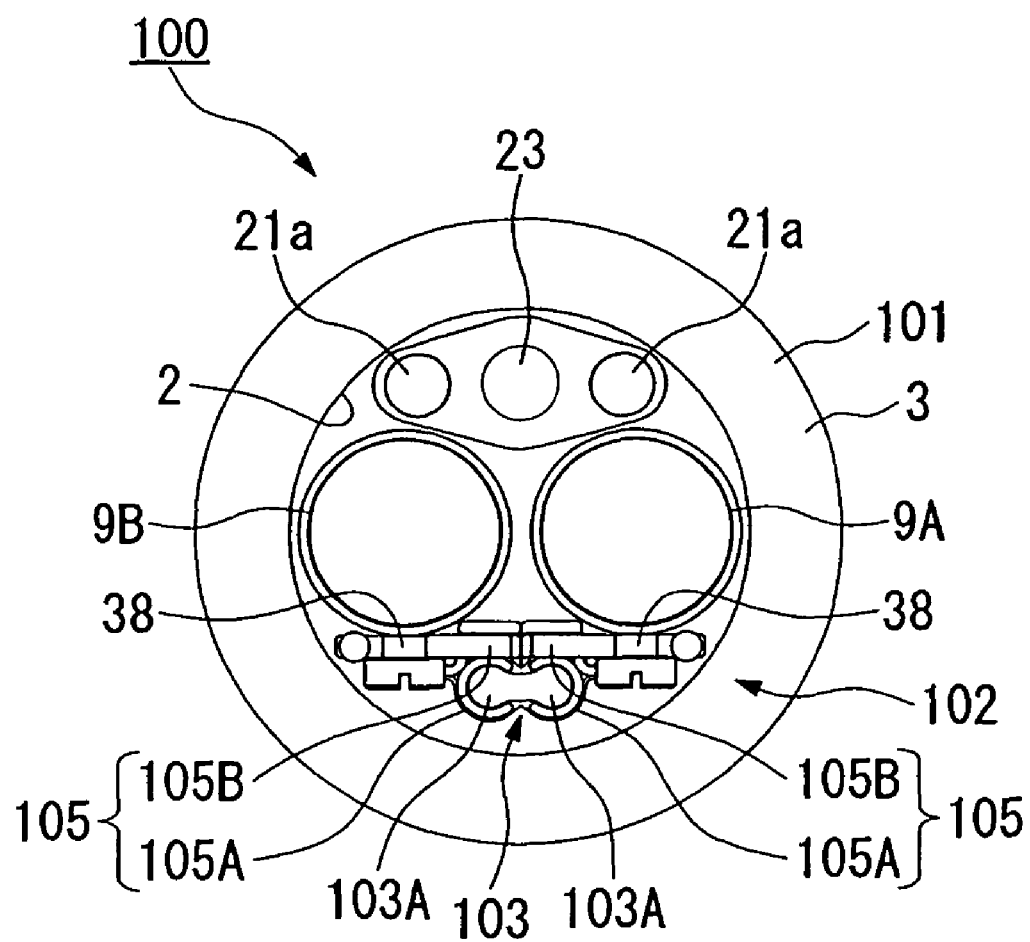
FIG. 21 is a view of the front end of the medical treatment endoscope according to the second embodiment.

Namely, as shown in FIG. 21, roughly cylindrical engaging convexities 103A are disposed to either end of a guide member 103 for an advance/retract mechanism 102, along the width direction of the guide member 103. The first arm member 8A and the second arm member 8B are connected to a sliding member 105 that has an engaging concavity 105A for engaging in a freely sliding manner with the engaging convexities 103A via a connector 105B.

As in the case of the moving frame 45A of the operating part 51 according to the first embodiment, this operating part is designed so that the open/close operating part 46 and the bending operating part 47 of not only the first arm member 8A, but also the second arm member 8B, are capable of movement with respect to the fixed frame.

Next, the effects of this embodiment will be explained. Note that the case when opening and closing the first arm member 8A and the second arm member 8B with respect to the sheath 101, the case when bending the first arm member 8A and the second arm member 8B, and the case when rotating the sheath 101, provide the same effects as those of the first embodiment.

The case when advancing or retracting the first arm member 8A and the second arm member 8B with respect to the sheath 101, as well, provides the same effects as in the case when advancing or retracting the first arm member 8A with respect to the fixed frame 45B in the first embodiment. In other words, when moving both the first arm member 8A and the second arm member 8B farther toward the front end side of the sheath 101, each of the moving frames of the operating part to which the first arm member 8A and the second arm member 8B are respectively connected is advanced with respect to the fixed frame. At this time, as in the first embodiment, the base at the operating part is advanced along the slide rail, while the sliding members 105 of the advance/retract mechanism 102 each advance with respect to the guide member 103. In this way, the first arm member 8A and the second arm member 8B are advanced with respect to the sheath 101.

On the other hand, when moving the first arm member 8A and the second arm member 8B toward the hand-held side of the sheath 101, the respective moving frames are retracted with respect to the fixed frame. At this time, the base is retracted along the slide rail, while the sliding members 105 are retracted with respect to the guide member 103. In this way, the first arm member 8A and the second arm member 8B are once again disposed at the starting state position.

The medical treatment endoscope 100 of this embodiment offers the same actions and effects as described in the first embodiment. In particular, since the first arm member 8A and the second arm member 8B are advanced and retracted with respect to the sheath 101, it is possible to ensure a wider line of vision V for the image pick-up unit 11. Furthermore, the approach angle for instruments such as gripping forceps and the like can be adjusted to a more suitable position. In addition, it is possible to increase the operating stroke for the gripping forceps, etc.

Note that the technical scope of the present invention is not limited to the preceding embodiments. Rather, various alterations may be applied provided they are within limits that do not depart from the spirit of the invention.

For example, the arm members are not limited to two; rather, three or more arm members may be provided. It is also acceptable to design the front end of the second arm member so as to enable relative displacement of the gripping forceps in the advancing/retracting direction with respect to the second arm member. In addition, while an illuminating member for radiating illuminating light on the target object was formed using the light guides 21A and 21B and an illuminating lens 21a, it is also acceptable to provide an illuminating member by disposing a light emitting element, an LED for example, to the sheath front end part 3A.

What is claimed is:

1. A medical treatment endoscope comprising:
   a sheath having a flexibility;
   an arm member having a bending part that projects out from a front end of the sheath and performs bending actions;
   an advance/retract mechanism which advances and retracts the arm member with respect to the sheath;
   an open/close mechanism which directs the arm member from a direction along a central axis of the sheath to a rotational direction deviated from the central axis of the sheath around a base axis of the arm member, and from the rotational direction deviated from the central axis of the sheath around the base axis of the arm member to a direction along the central axis of the sheath; and
   a viewing device and an illuminating member that are disposed to the front end side of the sheath; and
   an operating member that is inserted in a freely advancing and retracting manner into the sheath;
   wherein the advance/retract mechanism includes:
   a guide part that is fixed to the distal end of the sheath;
   a slide part that is capable of advancing and retracting with respect to the sheath and the guide part, is restricted in an amount of movement thereof with respect to the guide part to predetermined limits, and is capable of protruding from a distal end of the sheath and the guide part in the direction of the arm member advancing/retracting; and
   the open/close mechanism includes:
   a first linking part and a second linking part, for converting the advance/retract mechanism of the operating member into the open/close mechanism due to the operating member advancing and retracting,
   wherein a distal end of the first linking part is connected to the arm member and the other end thereof is connected to the slide part, and a distal end of the second linking part is fixed to another arm member and the other end thereof is fixed to the guide part.

2. The medical treatment endoscope according to claim 1, wherein a front end of the arm member is capable of relative displacement with respect to the viewing device and the illuminating member by means of at least one of a bending action of the bending part and a directional transition of the arm member by the open/close mechanism.

3. The medical treatment endoscope according to claim 2, including an operating part having:
   a frame;
   an open/close operating part for advancing and retracting the open/close operating member; and
   a bending operating part to which a procedure operating part for a procedure device for performing a procedure in an organ is attachable, for bending the bending part.

4. The medical treatment endoscope according to claim 3, wherein the operating part further includes a rotation operating part that rotatably connects a base end of the sheath with respect to the frame.

5. The medical treatment endoscope according to claim 1, wherein the operating part includes an advance/retract operating part for operating the advance/retract mechanism.

6. The medical treatment endoscope according to the claim 1, further comprising a rotational axis to rotate the arm member, away from the central axis of the arm, arranged in an orthogonal direction with respect to an axis which is paralleled to the direction of the central axis of the arm member.

7. The medical treatment endoscope according to the claim 1, wherein one or more of the first and second linking parts has a simple joint.

8. The medical treatment endoscope according to the claim 1, wherein a rotation of the arm member is regulated by advancing and retracting the arm member with respect to the sheath.

9. The medical treatment endoscope according to the claim 1, wherein
   the viewing device is fixed to the distal end of the sheath, and
   the open/close mechanism makes the arm member open and close in a position anterior to the viewing device.

10. The medical treatment endoscope according to claim 1, wherein the arm member and the two linking parts advance and retract on axial line of the sheath.

\* \* \* \* \*